US012582810B2

(12) United States Patent
Skak et al.

(10) Patent No.: US 12,582,810 B2
(45) Date of Patent: Mar. 24, 2026

(54) DELIVERY DEVICE FOR ORAL DELIVERY OF DRUG SUBSTANCES

(71) Applicant: Biograil ApS, Rosklide (DK)

(72) Inventors: Nikolaj Skak, Haslev (DK); Karsten Lindhardt, Haslev (DK)

(73) Assignee: Biograil ApS, Rosklide (DK)

( * ) Notice: Subject to any disclaimer, the term of this patent is extended or adjusted under 35 U.S.C. 154(b) by 851 days.

(21) Appl. No.: 17/759,607

(22) PCT Filed: Jan. 29, 2021

(86) PCT No.: PCT/EP2021/052100
§ 371 (c)(1),
(2) Date: Jul. 27, 2022

(87) PCT Pub. No.: WO2021/152085
PCT Pub. Date: Aug. 5, 2021

(65) Prior Publication Data
US 2023/0086298 A1 Mar. 23, 2023

(30) Foreign Application Priority Data

Jan. 29, 2020 (DK) .............................. PA202070055

(51) Int. Cl.
*A61M 31/00* (2006.01)
(52) U.S. Cl.
CPC .................................. *A61M 31/002* (2013.01)
(58) Field of Classification Search
CPC .................................................... A61M 31/002
See application file for complete search history.

(56) References Cited

U.S. PATENT DOCUMENTS

| | | |
|---|---|---|
| 2004/0220660 A1 | 11/2004 | Shanley et al. |
| 2011/0112513 A1* | 5/2011 | Hester .................. A61B 17/083 |
| | | 606/228 |
| 2011/0125091 A1* | 5/2011 | Abbate ................. A61M 31/00 |
| | | 606/199 |
| 2017/0258833 A1 | 9/2017 | Imran et al. |

FOREIGN PATENT DOCUMENTS

| | | |
|---|---|---|
| KR | 2012/0041630 A | 5/2012 |
| TW | 201536363 A | 10/2015 |
| WO | WO 2006/007473 A1 | 1/2006 |
| WO | WO 2010/126912 A1 | 11/2010 |

(Continued)

OTHER PUBLICATIONS

International Search Report and Written Opinion for International Application No. PCT/EP2021/052100 mailed Jun. 30, 2021, 16 pages.

(Continued)

*Primary Examiner* — Bradley J Osinski
(74) *Attorney, Agent, or Firm* — KNOBBE, MARTENS, OLSON & BEAR, LLP

(57) ABSTRACT

The present disclosure relates to a delivery device (2) capable of delivering payload to an internal surface of a subject. In some embodiments, the delivery device may deliver payload to the gastrointestinal tract. In some embodiments, the compositions contain active drug substances. In some embodiments, the active drug substances are low permeable active drug substances.

18 Claims, 24 Drawing Sheets

(56)     References Cited

FOREIGN PATENT DOCUMENTS

| | | |
|---|---|---|
| WO | WO 2010/132648 A1 | 11/2010 |
| WO | WO 2013/003824 A1 | 1/2013 |
| WO | WO 2018/191527 A1 | 10/2018 |
| WO | WO 2019/002277 A1 | 1/2019 |
| WO | WO 2019/071178 A2 | 4/2019 |
| WO | WO 2019/121686 A1 | 6/2019 |

OTHER PUBLICATIONS

First Technical Examination and Search Report for Danish Application No. PA202070055 mailed Jul. 9, 2020, 8 pages.

* cited by examiner (bare) Resoloy needle: 0h in flowing PBS          Gold coated Resoloy needle : 0h in flowing PBS (bare) Resoloy needle: 2h in flowing PBS          Gold coated Resoloy needle : 2h in flowing PBS Results:

| Nr | R_{p0.2} MPa | R_m MPa | A % |
|----|------|-----|------|
| 1 | 131 | 212 | 21.5 |
| 2 | 122 | 217 | 29.8 |
| 3 | 131 | 217 | 28.4 |

Chart:

Results:

| Nr | $R_{p0.2}$ MPa | $R_m$ MPa | $A$ % |
|----|------|------|------|
| 1 | 214 | 282 | 34,0 |
| 2 | 215 | 281 | 28,3 |
| 3 | 217 | 282 | 29,3 |

Chart:

Results:

| Nr | $R_{p0.2}$ MPa | $R_m$ MPa | $A_t$ % |
|----|------|------|------|
| 1 | 220 | 317 | 21,8 |
| 2 | 232 | 317 | 19,5 |
| 3 | 223 | 313 | 18,9 |

Chart:

DELIVERY DEVICE FOR ORAL DELIVERY OF DRUG SUBSTANCES

The present disclosure relates to a delivery device capable of oral delivery of drug substances. In some embodiments, the delivery device may deliver drug substances or compositions to the gastrointestinal tract.

BACKGROUND

A number of low permeable active drug substances are currently delivered by subcutaneous, intradermal, intramuscular or intravenous routes. Oral administration has the potential for the widest patient acceptance thus attempts to deliver low permeable active drug substances through the preferred oral route of administration has been tried but with limited success. This is mainly due to two things. Lack of stability and limited absorption from the gastrointestinal tract.

Stability both relates to the stability of the active drug substance during manufacturing and storage of the delivery device, and to the stability of the active drug substance during the passage in the gastrointestinal tract before it become available for absorption.

Limited gastrointestinal absorption is due to the gastrointestinal wall barrier preventing active drug substance from being absorbed after oral dosing because of the low permeability of the active drug substance, which is for example due to pre-systemic metabolism, size and/or the charges and/or because of the water solubility of the active drug substance.

Multiple approaches to solve these stability and absorption challenges have been suggested, but an effective solution to the challenges remain unresolved. Especially, where the delivery device is stable and at the same time facilitate effective absorption from the gastrointestinal tract after oral administration. It will be beneficial to promote delivery devices suitable for such use through the oral route.

Thus, there is an unmet need to provide a novel delivery device, which is capable of delivering stable low permeable active drug substances for absorption in the gastrointernal tissue. More generally, there remains a need for delivery devices and methods that enable enhanced drug delivery, when delivery devices are administered orally to patients.

SUMMARY

A delivery device for a composition is disclosed. The delivery device may have a first end and a second end with a longitudinal axis there between, and may comprise a body and a delivery part, the body may extend along a body axis from a first body end and may have a body surface. The delivery part may comprise one or more attachment parts including a first attachment part, the first attachment part may have a first distal end, e.g. configured to position and/or attach the delivery part in an internal surface of a subject.

Also disclosed is a pharmaceutical composition comprising a carrier and one or more delivery devices as described herein. In some embodiments, the delivery device may be administered orally. In some embodiments, the delivery device may provide an improved delivery of for example low permeable active drug substances in particular for oral delivery.

A first attachment part made of material comprising one or more of magnesium, iron and zinc allows for accurate and precise control of the size and/or shape/geometry of the first attachment part in turn allowing for a delivery device with desired attachment capabilities and/or small production variances which is in particular important in the pharmaceutical industry.

Further, a delivery device that is suitable for oral administration and in particular for attachment to an internal surface of a subject is provided.

In some embodiments, the delivery device, such as the body and/or attachment part(s), may comprise one or more barb elements. A barb element may assist in keeping the attachment part/delivery device secured or attached to the internal surface.

In some embodiments, the delivery device may comprise a delivery part constructed to carry and/or protect a payload. In some embodiments, the delivery device may comprise a delivery part constructed to protect a payload through to the gastrointestinal tract by carrying the payload from the stomach to the intestinal lumen into the intestinal wall.

In some embodiments, the delivery device may be constructed in a way that secures the adapted delivery part to deliver its payload into the internal tissue or internal surface for distribution of the active drug substance in the subject through the blood vessels.

In some embodiments, bowel movements may provide the physical forces generated by the musculature in and around the gastrointestinal tract to facilitate the correct positioning of the delivery device in the gastrointestinal tract and to comprise the physical force needed to position the delivery part into the intestinal wall to release the active drug substance in the gastrointestinal tissue.

In some embodiments, the force applied to the delivery device for example the device body from the peristaltic forces can either be dragging or pushing the delivery part into the gastrointestinal tissue.

In some embodiments, the delivery device utilizes the peristaltic forces posterior to the delivery part to drag the attachment part into the gastrointestinal tissue and/or utilization of peristaltic forces anterior to the delivery part to push the delivery part into the gastrointestinal tissue by utilizes the device body.

In some embodiments, the transport of the active drug substance across the gastrointestinal wall may be localized at the site of attachment in the gastrointestinal tract and consequently this will be the site of release of the active drug substance.

BRIEF DESCRIPTION OF THE FIGURES

The above and other features and advantages of the present disclosure will become readily apparent to those skilled in the art by the following detailed description of exemplary embodiments thereof with reference to the attached drawings, in which.

DETAILED DESCRIPTION

Figure 1:
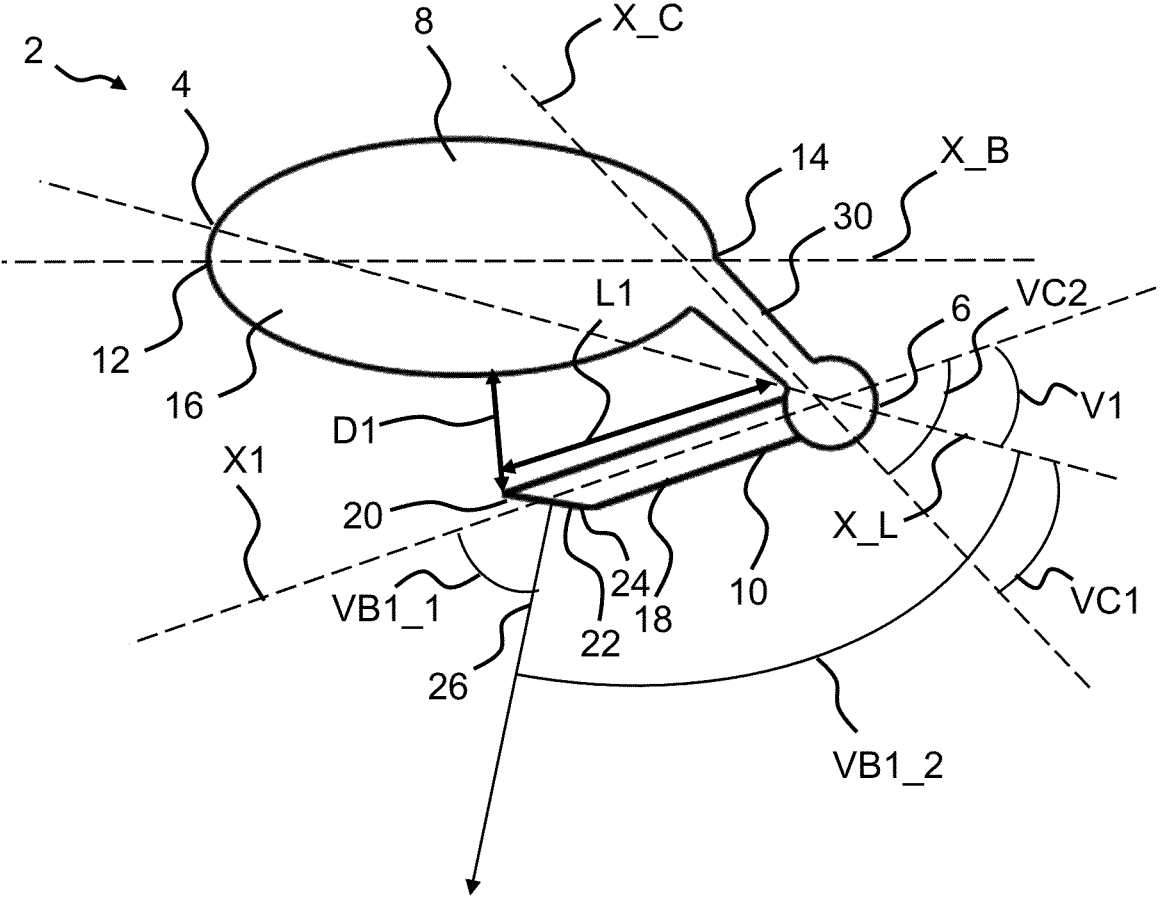
FIG. 1 schematically illustrates an exemplary delivery device

A delivery device used according with the present disclosure may, in theory, be of any shape or design.

The Delivery Device

The present disclosure relates to a delivery device for a composition. The composition may contain an active drug substance.

In some embodiments, the delivery device for a composition, may have a first end and a second end, with a longitudinal axis there between, and may comprise a body and a delivery part, the body may extend along a body axis from a first body end and may have a body surface, the delivery part may comprise a first attachment part, the first attachment part may have a first distal end configured to position the delivery part in an internal tissue of a subject. The first distal end may be arranged at a distance from the body surface. The distance may be at least 0.5 mm.

Internal Tissue/Internal Surface

In some embodiments, internal tissue or internal surface refers to cells, tissue, including mucosal tissues, vascular tissues, lymphatic vessels, gastrointestinal (GI) tissue, vaginal tissue, and cell membranes internal to a subject (for example a human or an animal). In some embodiments, the internal tissue is in an organ selected from the gastrointestinal tract selected for example from the esophagus, stomach, duodenum, small intestine, caecum, large intestine, colon, rectum. In some embodiments, the internal tissue is in the internal gastrointestinal tract.

In some embodiments, the delivery device size and geometry including the body and the delivery part may be designed to fit into a pharmaceutical composition.

In some embodiments, the delivery device size and geometry including the body and the delivery part may be designed to fit into a pharmaceutical composition for oral administration.

Dimension

In some embodiments, the greatest dimension or at least one dimension of the delivery device may be about or less than about 30 mm, about 25 mm, about 20 mm, about 15 mm, about 10 mm, about 7 mm, about 4 mm, or even about 2 mm. In some embodiments, the greatest dimension or at least one dimension of the delivery device may be more than about 2 mm, about 5 mm, about 10 mm, about 15 mm, about 20 mm, or about 25 mm. In some embodiments, the greatest dimension or at least one dimension of the delivery device may be within a range of about 6 mm to about 23 mm. In some embodiments, the dimensions of the delivery devices may be represented by a length, a width or a height in X, Y and Z axis where each dimension may be within a range of about 3 mm to about 26 mm in the length, of about 1 mm to about 12 mm in the width and of about 1 mm to about 12 mm in the height.

Material

In some embodiments, the delivery device, the body and/or the delivery part may comprise one or more of for example water-soluble, water-insoluble, biodegradable, non-biodegradable and/or pH-dependent soluble materials.

In some embodiments, water soluble material may allow immediate dissolution or controlled dissolution of the body depending on the material selected. In some embodiments, water insoluble and/or biodegradable material may preserve the body shape throughout the passage though the gastrointestinal tract. In some embodiments, pH dependent soluble material may allow the body to stay intact at pH conditions below the pH at which the material may dissolve for example in the stomach or upper intestinal lumen, but then to dissolve in the upper or lower intestinal lumen after detachment of the delivery part inside the intestinal wall at pH conditions above the pH at which the material dissolves.

In some embodiments, the delivery device may substantially be insoluble in an aqueous medium. In some embodiments, the body may be insoluble to an aqueous medium, such as water. In some embodiments, the delivery part may be insoluble to an aqueous medium, such as water. This ensures that the payload may only be in contact with surrounding aqueous media by one or more openings in the delivery part.

In some embodiments, the delivery device may be biodegradable, disintegrate, crumble or dissolve during the release of the active drug substance. In some embodiments, the delivery part may be biodegradable, disintegrate, crumble or dissolve during the release of the active drug substance. In some embodiments, the body may be biodegradable, disintegrate, crumble or dissolve during the release of the active drug substance.

In some embodiments, the delivery device may be applied for delivery of the active drug substance and may remain intact if it is supported by the payload containing the active drug substance. In some embodiments, the delivery device may lack the ability to remain intact after the payload has delivered the active drug substance. In some embodiments, the delivery device may not remain in the subject for any significant amount of time after completed the delivery of the active drug substance.

In some embodiments, the delivery device, e.g. body and/or delivery part, may contain polymers, plasticizers, pharmaceutical acceptable excipients, enhancers, adhesive material, surfactant, release modifier, stabilizers to improve chemical and physical stability such as for example antioxidants, pH regulators, aggregation reductants and/or chelators. Further details of the materials used is also described below in the General production materials section.

The Body

In some embodiments, the delivery device may be made of a material comprising one or more thermoplastic polymers. In some embodiments, the delivery device may be reinforced by fibers or similar.

The delivery device may comprise a body. In some embodiments, the body may be made of a material comprising one or more thermoplastic polymers. In some embodiments, the body may have a shape and size assisting in positioning the delivery part (attachment part(s)) in a suitable angle and position to ensure that the distal end(s) of the attachment part(s) to position in the internal surface of the subject, such that the delivery part may be attached to the internal surface for example for delivery of an active drug substance through the internal surface. In other words, the body may be constructed such that secure attachment of attachment part(s) to the internal surface, for example tissue of the gastrointestinal wall, may be provided, thus allowing the delivery device to deliver payload or an active drug substance in the internal tissue.

Figure 15:
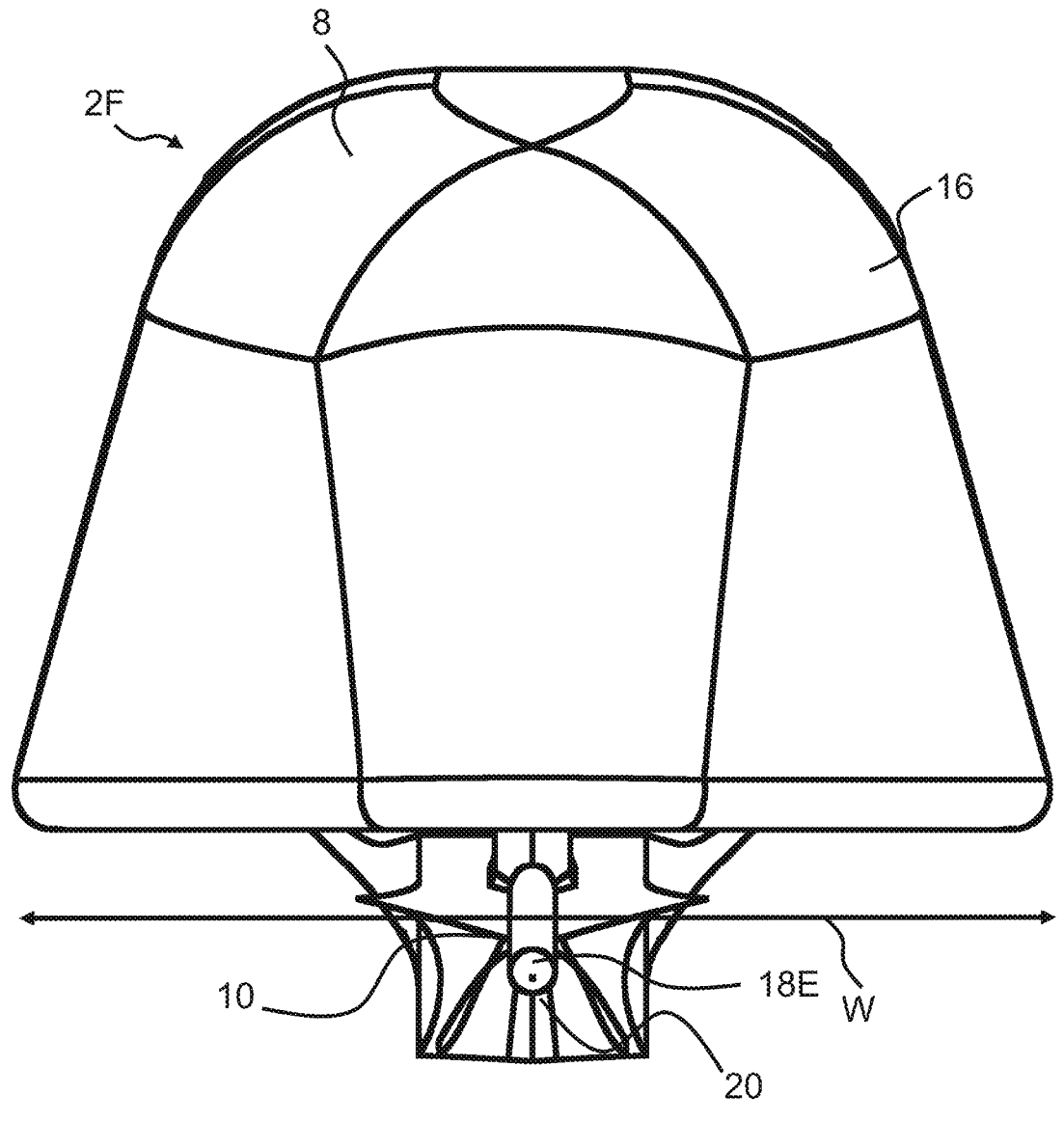
FIG. 15 is a view of an exemplary delivery device

The body may have a dome shaped or curved outer surface part facing away from the first attachment part and optionally a substantially planar surface part facing the first attachment part e.g. as illustrated in FIG. 15.

In some embodiments, the body may have droplet shape with a wide end towards the first body end. Thus, the body may have a decreasing cross-sectional extension (largest extension perpendicular to the body axis) from a first point at a first body distance from the first body end. The body may have a first cross-sectional extension at the first point in the range from 1 mm to 15 mm, such as in the range from 2 mm to 15 mm, such as in the range from 2 mm to 14 mm, such as in the range from 2 mm to 13 mm, such as in the range from 2 mm to 12 mm, such as in the range from 2 mm to 11 mm, such as in the range from 2 mm to 10 mm, such as in the range from 2 mm to 9 mm, such as in the range from 2 mm to 8 mm such as in the range from 2 mm to 7 mm, such as in the range from 3 mm to 7 mm, for example with the first body distance being in the range from 1 mm to 15 mm, such as in the range from 2 mm to 15 mm, such as in the range from 2 mm to 14 mm, such as in the range from 2 mm to 13 mm, such as in the range from 2 mm to 12 mm, such as in the range from 2 mm to 11 mm, such as in the range from 2 mm to 10 mm, such as in the range from 2 mm to 9 mm, such as in the range from 2 mm to 8 mm such as in the range from 2 mm to 7 mm, such as in the range from 3 mm to 7 mm.

In some embodiments, the body may have a maximum cross-sectional extension along the body axis in the range from 1 mm to 15 mm, such as in the range from 2 mm to 15 mm, such as in the range from 2 mm to 14 mm, such as in the range from 2 mm to 13 mm, such as in the range from 2 mm to 12 mm, such as in the range from 2 mm to 11 mm, such as in the range from 2 mm to 10 mm, such as in the range from 2 mm to 9 mm, such as in the range from 2 mm to 8 mm such as in the range from 2 mm to 7 mm, such as in the range from 3 mm to 7 mm.

Figure 5:
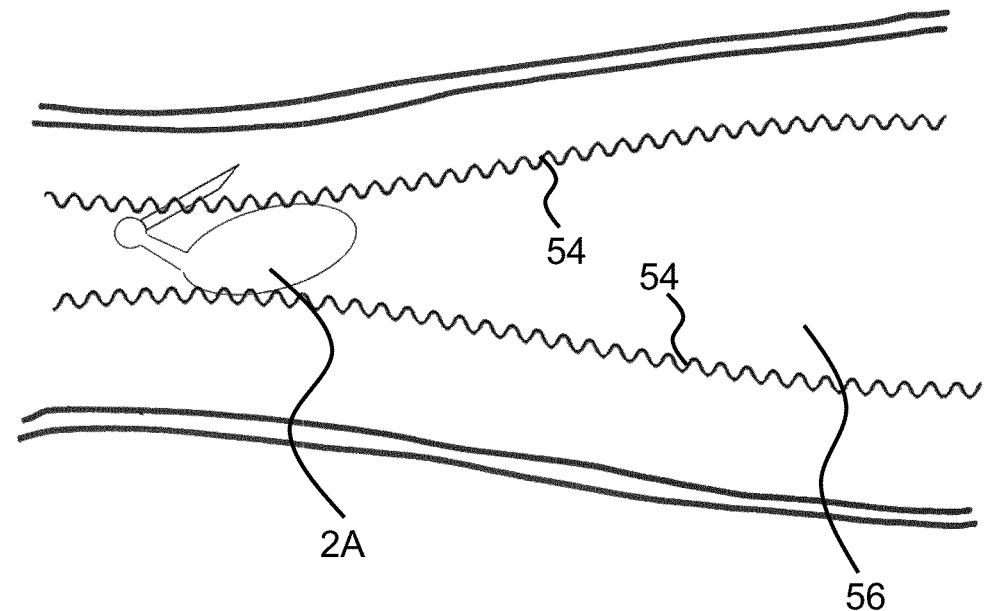
FIG. 5 illustrates a delivery device in a gastrointestinal environment

In some embodiments, the body of the delivery device may be constructed to secure the delivery part to deliver the payload into the gastrointestinal tissue of a subject. In some embodiments, the body size and shape of the delivery device may be designed in a way that bowel movements impact the position of the body, so that the body may be aligned in the gastrointestinal tract at the time of position the delivery part in the gastrointestinal wall and positions inside the gastrointestinal wall in a safe and reproducible manner. In some embodiments, the body size and shape of the delivery device may also be designed in a way that the forces from bowel movements has an impact on the body that secures appropriate directed force is put into the delivery part for it to position itself in the gastrointestinal wall, as illustrated in FIG. 5, which shows the delivery device in a gastrointestinal lumen.

In some embodiments, various body designs of the delivery device may achieve a reproducible release of the payload from the delivery part in the gastrointestinal tissue. In some embodiments, the body may for example be round, squared, triangular, cylindric, oval or curved shape. In some embodiments, the body may be flat for example like a patch. In some embodiments, the body may have attached hook(s) and/or barb(s) on the flat surface or in the perimeter of the edges for efficient anchor to the gastrointestinal wall, to secure alignment and optimal forces to be directed into the delivery part for it to position itself in the gastrointestinal wall.

In some embodiments, the body may contain a delivery part with one or more barbs to secure the same position of the body at the site of position the delivery part in the gastrointestinal wall for the time required for the delivery part to detach or for the payload from the delivery part to be released in the gastrointestinal tissue or for the payload from the body to be delivered through the delivery part. In some embodiments, the body may contain one or more barbs.

Connection Part

In some embodiments, the delivery device may comprise a connection part arranged between the body and the delivery part. The connection part may extend along a connection axis. The connection axis may form a first connection angle with the longitudinal axis. The first connection angle may be in the range from 30 degrees to 60 degrees. In some embodiments, the connection axis may form a second connection angle with the first axis. The second connection angle may be larger than 45 degrees, such as larger than 60 degrees. In some embodiments, the connection part may be strengthened, for example by thickening the connection part, to secure prolonged attachment of the delivery part to the body after the delivery part is positioned in the inner gastrointestinal wall.

In some embodiments, the connection part and the first distal end of the delivery part may control the depth of which the delivery part position itself in the inner gastrointestinal wall. In some embodiments, the length of the connection part may control the depth of which the delivery part is positioned in the inner gastrointestinal wall.

The Delivery Part

The delivery device comprises a delivery part. The delivery part may be configured to deliver a composition or a substance, such as an active drug substance, in an internal surface of the subject. In some embodiments, the delivery part may refer to a protruding shape from the delivery device. In some embodiments, the shape of the delivery part may be designed to secure reproducible penetration of the delivery part from the internal lumen into the internal tissue for example the inner gastrointestinal lumen into the gastrointestinal wall, without penetrating the outer internal tissue for example the outer gastrointestinal wall. In some embodiments, the shape of the delivery part may be designed to reproducibly attach to the internal tissue for example the gastrointestinal wall and once attached for example remain attached, detach or break from the body in such a way that the delivery part may remain inside the internal tissue for example gastrointestinal tissue until the payload may be released. In some embodiments, the shape of the delivery part may be designed to secure minimal physical impact on the internal tissue for example the inner gastrointestinal wall in such a way that the delivery device may be safe to administrate for the subject.

The delivery part may comprise a payload part and/or one or more attachment parts. In one or more exemplary delivery devices, the payload part is made of a first material and the attachment part(s), e.g. the first attachment part, is/are made of a second material different from the first material. The payload part may comprise one or more cavities for accommodating an active drug substance/payload.

In some embodiments, the delivery device may be arranged and constructed so that two or more delivery parts may protrude in different directions in the three-dimensional space. In some embodiments, the delivery part may protrude from the delivery device at an angle below 90 degrees.

In some embodiments, the delivery part may protrude at angle from a body surface, the delivery part may have a base integrally connected to the surface of the body.

In some embodiments, the shape of the delivery part may be bended/curved and/or rounded in such a way that it may be able to position itself in the internal tissue for example the gastrointestinal wall.

In some embodiments, the delivery part may protrude from the delivery device at an angle below 90 degrees to allow the delivery part to be longer than the thickness of the internal tissue for example the gastrointestinal wall.

The delivery part is made of material comprising one or more of magnesium, iron and zinc. In one or more exemplary delivery devices, the delivery part can include further elements as well. For example, the delivery part can include one or more of dysprosium and/or neodymium and/or europium and/or zirconium. The material of the delivery part may be biocompatible and/or biodegradable such as a biocompatible material and/or a biodegradable material.

Some of, part of, most of, substantially all, or all of the material of the delivery part may be biocompatible and/or biodegradable. The material of the delivery part may comprise, consist of, or essentially consist of, biocompatible and/or biodegradable material such as biocompatible and/or biodegradable metals. The material of the delivery part may comprise a biodegradable or bioresorbable metal or metal alloy, such as magnesium, zinc, and/or iron or an alloy comprising one or more of magnesium, zinc and iron. A biodegradable or bioresorbable metal or metal alloy may be understood as a metal or metal alloy that degrades safely within a body, such as a human body, in a practical amount of time, for example related to their application. The material of the delivery part may comprise one or more metals such as a combination of one or more metals e.g. as a metal alloy. An advantage of having a biodegradable material may be that the delivery device is able to deliver an active drug substance or payload arranged in the delivery part and/or body of the delivery device at a specific part of the body of the subject, e.g. such as the intestines after the delivery device has attached to the internal surface, e.g. the intestinal wall, thanks to the sharp properties of the material of the delivery part, and for an extended period of time, since the biodegradable material will degrade gradually in time. Further, when the material of the delivery part is biodegradable, the delivery part will degrade in the human body and disappear after having delivered the payload/active drug substance comprised in the delivery device, thereby avoiding harming the human subject over time. The delivery part may be configured to degrade in a period of time of hours, e.g. 2 hours, 5 hours, 10 hours, 20 hours, or 24 hours, days, e.g. 1 day, 2 days, 5 days, or weeks, e.g. 1 week, 2 weeks, 3 weeks, or 5 weeks.

The material of the delivery part may comprise one or more or a combination of magnesium (Mg), zinc (Zn), and/or iron (Fe). An advantage of having the delivery part of a material comprising Mg, Zn, and/or Fe may be that the shape and size of the delivery part can be precisely controlled thereby providing improved attachment to the internal surface, for example to an internal wall of the intestines of the human subject. In one or more exemplary delivery devices, the delivery part can include further elements as well. For example, the delivery part can include one or more of dysprosium (Dy) and/or neodymium (Nd) and/or europium (Eu) and/or zirconium (Zr).

For example, the material of the delivery part may comprise 0.001 wt % to 100 wt % of biodegradable metal such as 0.001 wt % to 100 wt % of magnesium, 0.001 wt % to 100 wt % of zinc, 0.001 wt % to 100 wt % of iron.

The material of the delivery part may for example comprise 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, 90 wt % of Mg, or 100 wt % of Mg. In one or more exemplary delivery devices, the delivery part may be magnesium based.

The material of the delivery part may for example comprise 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, 90 wt % of Zn, or 100 wt % of Zn.

The material of the delivery part may for example comprise 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, 90 wt % of Fe, or 100 wt % of Fe.

The material of the delivery part may comprise a metal alloy such as Zn—Mg, Zn—Fe, Mg—Fe, or Zn—Mg—Fe.

The material of the delivery part may for example comprise an alloy of Zn—Mg with 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, or 90 wt % of Mg. The alloy may have 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, or 90 wt % of Zn.

The material of the delivery part may for example comprise an alloy of Zn—Fe with 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, or 90 wt % of Fe. The alloy may have 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, or 90 wt % of Zn.

The material of the delivery part may for example comprise an alloy of Mg—Fe with 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, or 90 wt % of Fe. The alloy may have 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, or 90 wt % of Mg.

The material of the delivery part may for example comprise an alloy of Zn—Mg—Fe with 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, 90 wt % of Fe, 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, 90 wt % of Mg, 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, or 90 wt % of Zn.

The material of the delivery part may for example comprise an alloy with 5.0-25.5 wt % dysprosium.

The material of the delivery part may for example comprise an alloy with 0.01-5.0 wt % neodymium and/or europium.

The material of the delivery part may for example comprise an alloy with 0.1-3.0 wt % zinc.

The material of the delivery part may for example comprise an alloy with 0.1-2.0 wt % zirconium.

The material of the delivery part may for example comprise an alloy with 1 ppm-0.4 wt % impurities.

The material of the delivery part may for example comprise an alloy with a balance of magnesium.

The material of the delivery part may for example comprise an alloy with 5.0-25.5 wt % dysprosium, 0.01-5.0 wt % neodymium and/or europium, 0.1-3.0 wt % zinc, 0.1-2.0 wt % zirconium, 1 ppm-0.4 wt % impurities, and a balance of magnesium.

In one or more exemplary delivery devices, the delivery part may partially or fully comprise RESOLOY®. In one or more exemplary delivery devices, the delivery part may partially or fully comprise ZK60. In one or more exemplary delivery devices, the delivery part may partially or fully comprise a Mg—Zn—Ca alloy.

In one or more exemplary delivery devices, the delivery part may be bare. In alternative delivery devices, the delivery part may be at least partially coated by a material. The delivery part may be partially coated by a material. The delivery part may be fully coated by a material.

In one or more exemplary delivery devices, the delivery part may be coated with gold (Au). The coating may pure gold. The coating may be pure gold with inevitable impurities. The coating may be 95%, 96%, 97%, 98%, 99%, or 100% gold. The coating may be greater than 95%, 96%, 97%, 98%, or 99% gold. The coating may be less than 95%, 96%, 97%, 98%, 99%, or 100% gold.

The gold coating may be homogenously applied. The gold coating may not be homogenously applied. The gold coating may be a few nanometers in thickness. The gold coating may have a thickness of 1, 2, 3, 4, 5, 6, 7, 8, 9, or 10 nanometers. The gold coating may have a thickness of greater than 1, 2, 3, 4, 5, 6, 7, 8, 9, or 10 nanometers. The gold coating may have a thickness of less than 1, 2, 3, 4, 5, 6, 7, 8, 9, or 10 nanometers.

For example, the gold may be sputtered onto the delivery part. The gold may be deposited in other methods as well, and the particular method is not limiting. In one or more exemplary delivery devices, the delivery part may be coated with a gold alloy.

The use of a gold coating may provide advantages to the delivery device. For example, the gold coating can increase the biodegradation of the delivery part. The degradation may occur due to an evolving of a corrosion layer (e.g., phosphates). The degradation may also occur due to a rising of pH via gold degradation. Thus, a delivery part coated in gold may have improved biodegradation than a bare delivery part.

In one or more exemplary delivery devices, the delivery part may be coated with another material For example, a noble metal can be coated onto the delivery part. Materials such as silver and/or nickel and/or platinum and/or gold and/or combinations thereof can be coated onto the delivery part. The coating may be a pure material. The coating may include inevitable impurities. The coating may be an alloy.

In one or more exemplary drug delivery devices, the gold coating may only cover a portion of the delivery part to create a coated section of the delivery part. As the gold coating can cause increased biodegradation, this coated section may create a weakness for breakage and/or expedite active drug substance release and/or blunt any sharp tips, such as the distal end of the delivery part, for safety.

The delivery part, such as a payload part of the delivery part, may be made of a material comprising one or more thermoplastic polymers. The material of the delivery part/payload part may comprise one or more active drug substances. Thus, an active drug substance may be embedded in the material of the delivery part/payload part.

In some embodiments, the delivery part may comprise for example water soluble, water insoluble, biodegradable, non-biodegradable and/or pH dependent soluble materials. In some embodiments, the delivery part may comprise a water soluble, biodegradable and/or pH-dependent material that may dissolve and/or degrade so that the delivery part lodged in the intestinal tissue may gradually degrade and/or dissolve. In some embodiments, the delivery part may comprise a water-soluble material to allow immediate release or modified release of the payload depending on the material selected. In some embodiments, a water insoluble or biodegradable material may allow depot of the payload in the delivery part for longer release duration (for example days, weeks or months). In some embodiments, a pH dependent soluble material may allow the delivery part to stay intact at pH conditions below the physiologic for example a pH of approximately 7.4 to remain intact in the gastrointestinal lumen, but then may dissolve once inside the gastrointestinal wall. In some embodiments, one or more water soluble, water insoluble, biodegradable and/or pH dependent materials may optionally be combined to control release of the active drug substance for example by diffusion or erosion of the delivery part for controlled release duration (for example minutes, hours, days, weeks, or months).

In some embodiments, the delivery part may be made from different compositions such as for example an outer part of the delivery part may be made of one composition and an inner core of the delivery part may be made from another composition. In some embodiments, the outer part and the inner core of the delivery part may be composed of for example a water soluble, a water insoluble, a biodegradable, and/or a pH dependent material. In some embodiments, one or more water soluble, water insoluble, biodegradable and/or pH dependent materials may be combined to control the release of the active drug substance from the payload once the delivery part may move its position from the lumen to the internal tissue for example the gastrointestinal lumen to the gastrointestinal tissue.

In one or more exemplary delivery devices, the distal tip of the delivery part may be a metal alloy. The remainder of the delivery part may be a biodegradable polymer. The biodegradable polymer may be polylactic acid (PLA). The delivery part can be manufactured through co-molding, though the particular manufacturing is not limiting.

Further details of the materials used is also described below in the general production materials section.

In some embodiments, the first attachment part comprises a first distal end (hooking zone) and a cutting zone. In some embodiments, the first distal end (hooking zone) of the delivery part/first attachment part may be sharp enough to ensure the delivery part/first attachment part hooks easily into the internal tissue for example the gastrointestinal wall, the first distal end may have an angle or curvature, so the delivery part facilitate this. Cutting zone of the delivery part/first attachment part may have a pointy sharpness, cutting edge and/or sharp edges to cut the tissue without rupture, and the steady zone of the delivery part may contain payload and/or a separation part.

In some embodiments, the dimensions of the delivery part may be designed for the particular way in which it may be used. Without wishing to be bound by any particular theory, parameters such as the length of the delivery part such as the distance between the delivery device surface where the delivery part protrudes from to the first distal end of the delivery part, and the shape/size of the delivery part (for example, gauge size/width, first distal end shape, etc.) may influence the interaction of the delivery part, and thus the efficiency of delivery of a payload.

In some embodiments, the sharpness of the delivery part/first attachment part/second attachment part may be balanced in such a way that it may have the ability or properties to position itself in the internal tissue for example into the gastrointestinal wall. In some embodiments, the delivery part may include a first distal end.

In some embodiments, a gauge (for example the largest cross section) of the delivery part may be about or less than about 10 mm, about 9 mm, about 8 mm, about 7 mm, about 6 mm, about 5 mm, about 4 mm, about 3 mm, about 2 mm, about 1 mm or even about 0.5 mm. In some embodiments, a gauge (for example the largest cross section) of the delivery part may be more than about 0.5 mm, about 1 mm, about 2 mm, about 3 mm, about 4 mm, about 5 mm, about 6 mm, about 7 mm, about 8 mm, about 9 mm or even about 10 mm. In some embodiments, a gauge (for example the largest cross section) of the delivery part may be within a range of about 0.5 mm to about 10 mm, about 0.5 mm to about 9 mm, about 0.5 mm to about 8 mm, about 0.5 mm to about 7 mm, about 0.5 mm to about 6 mm, about 0.5 mm to about 5 mm, about 0.5 mm to about 4 mm, about 0.5 mm to about 3 mm, about 1 mm to about 3 mm.

In some embodiments, the delivery part may contain one or more protruding barbs to secure the same position of the delivery part and/or fix the delivery part in the internal tissue for the time required for the payload to be released in the internal tissue.

In some embodiments, the delivery part may be tubular and may include a tubular body and the tubular body may comprise a payload for example a liquid payload connected to a tubular delivery part so the payload may flow though the delivery part into the internal tissue for example the intestinal tissue. In some embodiments, the tubular body may contain expandable excipients that may expand by a chemical reaction for example when mixed expand in volume and/or produce a gas to advance the delivery of the payload. In some embodiments, the expansion is by osmosis.

In some embodiments, the delivery part may contain one or more enhancers and/or one or more adhesive materials to disrupt the internal tissue for example the inner gastrointestinal wall and release the active drug substance in the periphery of the internal tissue for example the inner gastrointestinal wall to provide access to the blood vessels in the internal tissue for example the gastrointestinal tissue.

In some embodiments, the length of the delivery part may be about or less than about 30 mm, about 29 mm, about 28 mm, about 27 mm, about 26 mm, about 25 mm, about 24 mm, about 23 mm, about 22 mm, about 21 mm, about 20 mm, about 19 mm, about 18 mm, about 17 mm, about 16 mm, about 15 mm, about 14 mm, about 13 mm, about 12 mm, about 11 mm, about 10 mm, about 9 mm, about 8 mm, about 7 mm, about 6 mm, about 5 mm, about 4 mm, about 3 mm, about 2 mm, about 1 mm or even about 0.5 mm.

In some embodiments, the length of the delivery part may be more than about 0.5 mm, about 1 mm, about 2 mm, about 3 mm, about 4 mm, about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, about 21 mm, about 22 mm, about 23 mm, about 24 mm, about 25 mm, about 26 mm, about 27 mm, about 28 mm, about 29 mm or even about 30 mm.

In some embodiments, the length of the delivery part may be within a range of about 0.5 mm to about 30 mm, about 1 mm to about 30 mm, about 1 mm to about 29 mm, about 1 mm to about 28 mm, about 1 mm to about 27 mm, about 1 mm to about 26 mm, about 1 mm to about 25 mm, about 1 mm to about 24 mm, about 1 mm to about 23 mm, about 1 mm to about 22 mm, about 1 mm to about 21 mm, about 1 mm to about 20 mm, about 1 mm to about 19 mm, about 1 mm to about 18 mm, about 1 mm to about 17 mm, about 1 mm to about 16 mm, about 1 mm to about 15 mm, about 1 mm to about 14 mm, about 1 mm to about 13 mm, about 1 mm to about 12 mm, about 1 mm to about 11 mm, about 1 mm to about 10 mm, about 0.5 mm to about 10.

In some embodiments, the delivery device may comprise a single attachment part. In some embodiments, the delivery device may comprise a plurality of attachment parts and may include two or more attachment parts. In some embodiments, the delivery device may comprise a first attachment part. In some embodiments, the delivery device may comprise a first attachment part and a second attachment part. In some embodiments, the delivery device may comprise a first attachment part, a second attachment part and a third attachment part etc.

First Attachment Part

The delivery part comprises a first attachment part. In some embodiments, the first attachment part may extend along a first axis. A first angle between the first axis and the longitudinal axis may be less than 75 degrees, such as in the range from 2 degrees to 60 degrees. In one or more exemplary delivery devices, the first angle is in the range from 5 degrees to 45 degrees. The first angle may be less than 20 degrees.

The first attachment part can be made of material comprising one or more of magnesium, iron and zinc. In one or more exemplary delivery devices, the first attachment part can include further elements as well. For example, the first attachment part can include one or more of dysprosium and/or neodymium and/or europium and/or zirconium. The material of the first attachment part may be biocompatible and/or biodegradable such as a biocompatible material and/or a biodegradable material.

Some of, part of, most of, substantially all of, or all of the material of the first attachment part may be biocompatible and/or biodegradable. The material of the first attachment part may comprise, consist of, or essentially consist of, biocompatible and/or biodegradable material such as biocompatible and/or biodegradable metal or metal alloys. The material of the first attachment part may comprise a biodegradable and/or bioresorbable metal, such as magnesium, zinc, and/or iron, or a biodegradable and/or bioresorbable metal alloy comprising one or more of magnesium, zinc, and iron. A biodegradable or bioresorbable metal or metal alloy may be understood as a metal or metal alloy that degrades safely within e.g. a human body in a practical amount of time, for example related to their application. The material of the first attachment part may comprise one or more metals such as a combination of one or more metals e.g. as a metal alloy. An advantage of having a biodegradable material may be that the first attachment part may deliver the payload/active drug substance comprised in the delivery device at a specific part of the body of the subject, e.g. such as the intestines after the first attachment part has attached to the internal surface, e.g. the intestinal wall, thanks to the sharp properties of the material of the first attachment part, and for an extended period of time, since the biodegradable material will degrade gradually in time. Further, when the material of the first attachment part is biodegradable, the first attachment part will degrade in the human body and disappear after having delivered the payload/active drug substance comprised in the delivery device, thereby avoiding harming the human subject over time. The first attachment part may be configured to degrade in a period of time of hours, e.g. 2 hours, 5 hours, 10 hours, 20 hours, or 24 hours, days, e.g. 1 day, 2 days, 5 days, or weeks, e.g. 1 week, 2 weeks, 3 weeks, or 5 weeks.

The material of the first attachment part may comprise one or more or a combination of magnesium (Mg), zinc (Zn), and/or iron (Fe). An advantage of having the first attachment part of a material comprising Mg, Zn, and/or Fe may be that the shape and size of the first attachment part can be precisely controlled, e.g. in a laser cutting process, thereby providing improved attachment to the internal surface, for example to an internal wall of the intestines of the human subject. In one or more exemplary delivery devices, the first attachment part can include further elements as well. For example, the first attachment part can include one or more of dysprosium (Dy) and/or neodymium (Nd) and/or europium (Eu) and/or zirconium (Zr).

For example, the material of the first attachment part may comprise 0.001 wt % to 100 wt % of biodegradable metal such as 0.001 wt % to 100 wt % of magnesium, 0.001 wt % to 100 wt % of zinc, 0.001 wt % to 100 wt % of iron.

The material of the first attachment part may for example comprise 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, 90 wt % of Mg, or 100 wt % of Mg. In one or more exemplary delivery devices, the first attachment part may be magnesium based.

The material of the first attachment part may for example comprise 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, 90 wt % of Zn, or 100 wt % of Zn.

The material of the first attachment part may for example comprise 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, 90 wt % of Fe, or 100 wt % of Fe.

The material of the first attachment part may comprise a metal alloy such as Zn—Mg, Zn—Fe, Mg—Fe, or Zn—Mg—Fe.

The material of the first attachment part may for example comprise an alloy of Zn—Mg with 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, or 90 wt % of Mg. The alloy may have 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, or 90 wt % of Zn.

The material of the first attachment part may for example comprise an alloy of Zn—Fe with 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, or 90 wt % of Fe. The alloy may have 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, or 90 wt % of Zn.

The material of the first attachment part may for example comprise an alloy of Mg—Fe with 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, or 90 wt % of Fe. The alloy may have 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, or 90 wt % of Mg.

The material of the first attachment part may for example comprise an alloy of Zn—Mg—Fe with 0.001 wt % of Fe, 0.005 wt % of Fe, 0.01 wt % of Fe, 0.05 wt % of Fe, 0.1 wt % of Fe, 0.5 wt % of Fe, 1 wt % of Fe, 5 wt % of Fe, 10 wt % of Fe, 20 wt % of Fe, 30 wt % of Fe, 40 wt % of Fe, 50 wt % of Fe, 60 wt % of Fe, 70 wt % of Fe, 80 wt % of Fe, 90 wt % of Fe, 0.001 wt % of Mg, 0.005 wt % of Mg, 0.01 wt % of Mg, 0.05 wt % of Mg, 0.1 wt % of Mg, 0.5 wt % of Mg, 1 wt % of Mg, 5 wt % of Mg, 10 wt % of Mg, 20 wt % of Mg, 30 wt % of Mg, 40 wt % of Mg, 50 wt % of Mg, 60 wt % of Mg, 70 wt % of Mg, 80 wt % of Mg, 90 wt % of Mg, 0.001 wt % of Zn, 0.005 wt % of Zn, 0.01 wt % of Zn, 0.05 wt % of Zn, 0.1 wt % of Zn, 0.5 wt % of Zn, 1 wt % of Zn, 5 wt % of Zn, 10 wt % of Zn, 20 wt % of Zn, 30 wt % of Zn, 40 wt % of Zn, 50 wt % of Zn, 60 wt % of Zn, 70 wt % of Zn, 80 wt % of Zn, or 90 wt % of Zn.

The material of the first attachment part may for example comprise an alloy with 5.0-25.5 wt % dysprosium.

The material of the first attachment part may for example comprise an alloy with 0.01-5.0 wt % neodymium and/or europium.

The material of the first attachment part may for example comprise an alloy with 0.1-3.0 wt % zinc.

The material of the first attachment part may for example comprise an alloy with 0.1-2.0 wt % zirconium.

The material of the first attachment part may for example comprise an alloy with 1 ppm-0.4 wt % impurities.

The material of the first attachment part may for example comprise an alloy with a balance of magnesium.

The material of the first attachment part may for example comprise an alloy with 5.0-25.5 wt % dysprosium, 0.01-5.0 wt % neodymium and/or europium, 0.1-3.0 wt % zinc, 0.1-2.0 wt % zirconium, 1 ppm-0.4 wt % impurities, and a balance of magnesium.

In one or more exemplary delivery devices, the first attachment part may partially or fully comprise RESO-LOY®. In one or more exemplary delivery devices, the first attachment part may partially or fully comprise ZK60. In one or more exemplary delivery devices, the first attachment part may partially or fully comprise a Mg—Zn—Ca alloy.

In one or more exemplary delivery devices, the first attachment part may be bare. In alternative delivery devices, the first attachment part may be at least partially coated by a material. The first attachment part may be partially coated by a material. The first attachment part may be fully coated by a material.

In one or more exemplary delivery devices, the first attachment part may be coated with gold (Au). The coating may pure gold. The coating may be pure gold with inevitable impurities. The coating may be 95%, 96%, 97%, 98%, 99%, or 100% gold. The coating may be greater than 95%, 96%, 97%, 98%, or 99% gold. The coating may be less than 95%, 96%, 97%, 98%, 99%, or 100% gold.

The gold coating may be homogenously applied. The gold coating may not be homogenously applied. The gold coating may be a few nanometers in thickness. The gold coating may have a thickness of 1, 2, 3, 4, 5, 6, 7, 8, 9, or 10 nanometers. The gold coating may have a thickness of greater than 1, 2, 3, 4, 5, 6, 7, 8, 9, or 10 nanometers. The gold coating may have a thickness of less than 1, 2, 3, 4, 5, 6, 7, 8, 9, or 10 nanometers.

For example, the gold may be sputtered onto the first attachment part. The gold may be deposited in other methods as well, and the particular method is not limiting. In one or more exemplary delivery devices, the first attachment part may be coated with a gold alloy.

The use of a gold coating may provide advantages to the delivery device. For example, the gold coating can increase the biodegradation of the first attachment part. The degradation may occur due to an evolving of a corrosion layer (e.g., phosphates). The degradation may also occur due to a rising of pH via gold degradation. Thus, a first attachment part coated in gold may have improved biodegradation than a bare first attachment part.

In one or more exemplary delivery devices, the first attachment part may be coated with another material For example, a noble metal can be coated onto the first attachment part. Materials such as silver and/or nickel and/or platinum and/or gold and/or combinations thereof can be coated onto the first attachment part. The coating may be a pure material. The coating may include inevitable impurities. The coating may be an alloy.

In one or more exemplary drug delivery devices, the gold coating may only cover a portion of the first attachment part to create a coated section of the first attachment part. As the gold coating can cause increased biodegradation, this coated section may create a weakness for breakage and/or expedite active drug substance release and/or blunt any sharp tips, such as the distal end of the first attachment part, for safety.

The first attachment part, such as a payload part of the first attachment part, may be made of a material comprising one or more thermoplastic polymers. The material of the first attachment part/payload part may comprise one or more active drug substances. Thus, an active drug substance may be embedded in the material of the first attachment part/payload part.

In some embodiments, the first attachment part may comprise for example water soluble, water insoluble, biodegradable, non-biodegradable and/or pH dependent soluble materials. In some embodiments, the first attachment part may comprise a water soluble, biodegradable and/or pH-dependent material that may dissolve and/or degrade so that the first attachment part lodged in the intestinal tissue may gradually degrade and/or dissolve. In some embodiments, the first attachment part may comprise a water-soluble material to allow immediate release or modified release of the payload depending on the material selected. In some embodiments, a water insoluble or biodegradable material may allow depot of the payload in the first attachment part for longer release duration (for example days, weeks or months). In some embodiments, a pH dependent soluble material may allow the first attachment part to stay intact at pH conditions below the physiologic for example a pH of approximately 7.4 to remain intact in the gastrointestinal lumen, but then may dissolve once inside the gastrointestinal wall. In some embodiments, one or more water soluble, water insoluble, biodegradable and/or pH dependent materials may optionally be combined to control release of the active drug substance for example by diffusion or erosion of the first attachment part for controlled release duration (for example minutes, hours, days, weeks, or months).

In some embodiments, the first attachment part may be made from different compositions such as for example an outer part of the first attachment part may be made of one composition and an inner core of the first attachment part may be made from another composition. In some embodiments, the outer part and the inner core of the first attachment part may be composed of for example a water soluble, a water insoluble, a biodegradable, and/or a pH dependent material. In some embodiments, one or more water soluble, water insoluble, biodegradable and/or pH dependent materials may be combined to control the release of the active drug substance from the payload once the first attachment part may move its position from the lumen to the internal tissue for example the gastrointestinal lumen to the gastrointestinal tissue.

In one or more exemplary delivery devices, the distal tip of the first attachment part may be a metal alloy. The remainder of the first attachment part may be a biodegradable polymer. The biodegradable polymer may be polylactic acid (PLA). The first attachment part can be manufactured through co-molding, though the particular manufacturing is not limiting.

In some embodiments, the first attachment part may extend along a first axis, wherein a first angle between the first axis and the body axis is less than 75 degrees. In some embodiments, the first attachment part may be needle-shaped, conical, cylindrical, tubular pyramid-shaped, star-shaped, spatula-shaped, bevel-shaped, taper point-shaped or a hook-shaped. In some embodiments, the first attachment part may be straight, curved or semi hook-shaped. In some embodiments, the first attachment part may take the form of a spike.

In some embodiments, the first attachment part may define a first cavity for accommodating an active drug substance. In one or more exemplary delivery devices, the first attachment part defines a first cavity for accommodating a payload comprising an active drug substance. In some embodiments, the delivery part comprising a first attachment part, the first attachment part may have a first distal end configured to position the delivery part in an internal tissue of a subject. In one or more embodiments, the first attachment part may have a first distal end configured to position itself in an internal surface of the subject. The internal surface may be a gastrointestinal surface.

In some embodiments, the first attachment part may have a length in the range from 1.0 mm to 20 mm, such as in the range from 2.0 mm to 10 mm. In one or more exemplary delivery devices, the first attachment part has a length in the range from 4.0 mm to 6.0 mm, or example about 5 mm.

In some embodiments, the first distal end may be arranged at a distance from the body surface, wherein the distance optionally is at least 0.5 mm. The distance between the first distal end and the body surface may be at least 0.8 mm, such as in the range from 0.9 mm to 20 mm. In one or more exemplary delivery devices, the distance between the first distal end and the body surface is in the range from 1.0 mm to 5.0 mm, for example about 1.5 mm. In some embodiments, the first distal end of the first attachment part may be arranged between the first body end and a second body end of the body.

In some embodiments, the first attachment part may have a first distal end configured to position itself in an internal surface of a subject. The first distal end may be arranged at a distance from the body surface, wherein the distance is at least 0.5 mm.

In some embodiments, the first attachment part may comprise a first bend near or within 2.0 mm from the first distal end. The first distal end may point in a first direction forming a first primary bend angle with the longitudinal axis. The first primary bend angle may be less than 75 degrees, such as in the range from 0 degrees to 60 degrees. In one or more exemplary delivery devices, the first primary bend angle is in the range from 1 degree to 30 degrees. The first direction may form a first secondary bend angle with the first axis. The first secondary bend angle may be less than 75 degrees, such as in the range from 1 degree to 60 degrees. In one or more exemplary delivery devices, the first primary bend angle is in the range from 5 degrees to 30 degrees.

In some embodiments, the first attachment part may comprise a first bevel surface forming a cutting edge, for example extending from or within a distance in the range from 0.5 mm to 2 mm from the first distal end. The cutting edge formed by the first bevel surface may be at or near, such as within 2.0 mm from, the first distal end. The first bevel surface may be a plane surface. The first bevel surface may be concave. The first bevel surface may have a first bevel normal. The first bevel normal may form a first primary bevel angle with the first axis. The first primary bevel angle may be larger 20 degrees. The first primary bevel angle may be in the range from 30 degrees to 60 degrees. The first bevel normal may form a first secondary angle with the longitudinal axis. The first secondary angle may be larger 45 degrees. In one or more exemplary first attachment parts, the first secondary angle may be less than 45 degrees.

In some embodiments, the first bevel surface may be concave. In some embodiments, the first attachment part may comprise a first bevel surface forming a cutting edge extending from the first distal end. In some embodiments, the first bevel surface may have a first bevel normal, the first bevel normal forming a first primary bevel angle with the first axis larger 20 degrees. In some embodiments, the first bevel normal forming a first secondary angle with the body axis larger 45 degrees.

In some embodiments, the first attachment part may comprise a second bevel surface forming a cutting edge at or near, such as within 2.0 mm from, the first distal end. In some embodiments, the second bevel surface may be concave.

In some embodiments, the second bevel surface forms a cutting edge, for example extending from or within a distance in the range from 0.5 mm to 2.0 mm from the first distal end. The cutting edge formed by the second bevel surface may be at or near, such as within 2.0 mm from, the first distal end. The second bevel surface may be a plane surface. The second bevel surface may be concave.

The first attachment part may have a star-shaped cross-section with three, four or more cutting edges formed by recesses or cut-outs in the first attachment part. In some embodiments, the attachment part is designed with focus on utilizing the efficient piercing, with a sharp attachment and further to improve the subsequent cutting following the initial piercing of the internal tissue, to facilitate efficient and full penetration of the delivery part into the internal tissue.

In some embodiments, the initial piercing was made efficient by reducing the attachment part tip angle making the attachment part point sharper, and the length of the narrow part of the attachment part was extended as much reasonable to secure efficient piercing even when piercing elastic internal tissue.

In some embodiments, the cutting was facilitated by adding one or more sharp edges expanding from the point of piercing closer to or even beyond the width of the attachment part to facilitate cutting an opening for easy penetration of the delivery part when constrictive and propulsive peristaltic forces are applied to the delivery part.

In some embodiments, the point sharpness of the delivery part may be defined as the force a delivery part first distal end may use to penetrate a well-defined film. In the present context, the point sharpness of the delivery part relates to the first distal end of the first attachment part.

The force may be compared with the force used by a hypodermic needle to penetrate the same film. In some embodiments, hypodermic needles such as, a 25 G, 18 G and 18 G blunt needle have been used as reference, as a 18 G blunt needle may be difficult to insert in the internal tissue for example intestinal wall and the normal 25 G and 18 G needle may be relatively easy to insert in the internal tissue for example intestinal wall.

In some embodiments, the point sharpness of the delivery part may be the first local maximum of the time/force curve which relates to the penetration of the first distal end through the film and the point sharpness of delivery part is measured in gram. The values may only be used relative to the reference needles values. In some embodiments, the point sharpness of the delivery part may be better than a 18 G blunt needle. In some embodiments, the point sharpness of the delivery part may at least be in the same range as a 25 G and a 18 G needle or less than a 25 G and a 18 G needle.

Second Attachment Part

In some embodiments, the delivery part may comprise a second attachment part, the second attachment part may have a second distal end configured to position itself in an internal surface of a subject. The second attachment part may extend along a second axis. A second angle between the second axis and the longitudinal axis may be less than 75 degrees, such as in the range from 2 degrees to 60 degrees. In one or more exemplary delivery devices, the second angle is in the range from 5 degrees to 45 degrees.

The material of the second attachment part may be the same as described above in relation to the first attachment part.

In some embodiments, the second attachment part, may have a second distal end configured to position itself in an internal surface of the subject. The internal surface may be a gastrointestinal surface.

In some embodiments, the second attachment part may have a length in the range from 1.0 mm to 20 mm, such as in the range from 2.0 mm to 10 mm. In one or more exemplary delivery devices, the second attachment part has a length in the range from 4.0 mm to 6.0 mm, for example about 5 mm.

In some embodiments, the second distal end may be arranged at a distance from the body surface, wherein the distance is at least 0.5 mm. The distance between the second distal end and the body surface may be at least 0.8 mm, such as in the range from 0.9 mm to 20 mm. In one or more exemplary delivery devices, the distance between the second distal end and the body surface is in the range from 1.0 mm to 5.0 mm, for example about 1.5 mm.

Cavities

In some embodiments, the delivery part or a portion of the delivery part may be solid or hollow. In some embodiments, the delivery part or a part of the delivery part may be porous or non-porous. In some embodiments, the delivery part or a part of the delivery part may be degradable or non-degradable.

In some embodiments, the delivery device may comprise or define one or more cavities for accommodating a separation part. The separation part may break upon attachment of the delivery part in the internal surface for separating the body and the delivery part.

In some embodiments, the delivery device may comprise a payload with the active drug substance. The payload may be accommodated in a cavity of the delivery device. The payload may be divided into a plurality of payloads accommodated in a plurality of cavities. In some embodiments, the payload may be included in a first cavity and a second cavity of the delivery device.

In some embodiments, the delivery device may comprise or define one or more cavities for accommodating a payload. The payload may comprise an active drug substance.

In some embodiments, the first attachment part defines a first cavity for accommodating a payload comprising an active drug substance. In some embodiments, the second attachment part defines a second cavity for accommodating a payload comprising an active drug substance.

Separation Part

In some embodiments, the delivery device may comprise a separation part arranged between the body and the delivery part. The separation part may optionally be configured to break upon attachment of the delivery part in the internal surface for separating the body and the delivery part upon attachment of the delivery part.

In some embodiments, the separation part may comprise a water soluble, biodegradable and/or pH-dependent material that dissolves and/or degrades so that the delivery part is released from the body from which it protrudes and may remain lodged in the internal tissue.

In some embodiments, the separation part may contain hydrophilic plasticizers leaching out of a cavity or cavities, resulting in decreased mechanical resistance and allowing detachment or cracking, or resulting in pore formation for faster dissolution of the separation part.

In some embodiments, the separation part may contain polymers, plasticizers, pharmaceutical acceptable excipients, enhancers, adhesive material, surfactant, release modifier, stabilizers to improve chemical and physical stability such as for example antioxidants, pH regulators, aggregation reductants and/or chelators.

Payload

The delivery device may comprise a payload. In some embodiments, the delivery part may be dimensioned and constructed to comprise or carry one or more payloads, such as medical payloads.

In some embodiments, the outer part of the delivery part may be without a payload. In some embodiments, the outer part of the delivery part may contain a payload. In some embodiments, the inner core of the delivery part may be without a payload. In some embodiments, the inner core of the delivery part may contain a payload.

In some embodiments, the payload may be contained in one or more cavities. The payload may comprise an active drug substance.

In some embodiments, the payload may be in different concentrations with one or more type of materials. In some embodiments, the payload may be in different concentrations with the same or other type of materials to differentiate the release of the active drug substance from each payload. In some embodiments, the outer part of the delivery part may act as a physical barrier to shield the payload in the inner core of the delivery part from the lumen for example the gastrointestinal lumen until the delivery part may be positioned in the internal tissue for example gastrointestinal tissue.

In some embodiments, the delivery part volume may be designed to contain a payload composition with an active drug substance to obtain a biologic or medical response.

In some embodiments, the delivery part may be dimensioned and constructed to comprise or carry one payload and in some embodiments more than one payload. In some embodiments, the delivery part may be hollow or porous constructed to carry a payload in small cavities. In some embodiments, the delivery part may contain a hollow and a channel that enables storage of a payload in one or more cavities in the device body.

In some embodiments, the payload may comprise pharmaceutical composition, medical composition or an active drug substance to be delivered into the internal tissue to release for example the active drug substance in the internal tissue for distribution of the active drug substance to the blood vessels in the tissue. The active drug substance may then be distributed by the blood vessels in the subject. In some embodiments, a payload may include a bioactive agent. In some embodiments, the payload may comprise excipients with specific properties such as for example osmotic, wicking, hygroscopic, effervescent, swelling and/or disintegration properties.

In some embodiments, the payload may contain polymers, plasticizers, pharmaceutical acceptable excipients, enhancers, adhesive material, surfactant, release modifier, stabilizers to improve chemical and physical stability such as for example antioxidants, pH regulators, aggregation reductants and/or chelators.

In some embodiments, the payload may be in a solid, a semisolid or a liquid form or a combination thereof. In some embodiments, a payload may be in a gas form, a liquid form, a solid form or combinations thereof.

In some embodiments, the volume of a payload may be about or less than about 200 µl, about 175 µl, about 150 µl, about 125 µl, about 100 µl, about 75 µl, about 50 µl, about 25 µl, about 20 µl, about 15 µl, about 10 µl, about 9 µl, about 8 µl, about 7 µl, about 6 µl, about 5 µl, about 4.5 µl, about 4 µl, about 3.5 µl, about 3 µl about 2.5 µl, about 2 µl, about 1.5 µl, about 1 µl, about 0.9 µl, about 0.8 µl, about 0.7 µl, about 0.6 µl, about 0.5 µl, about 0.4 µl, about 0.3 µl, about 0.2 µl, about 0.1 µl, about 0.05 µl or even about 0.01 µl.

In some embodiments, the volume of a payload may be more than about 0.01 µl, about 0.05 µl, about 0.1 µl, about 0.2 µl, about 0.3 µl, about 0.4 µl, about 0.5 µl, about 0.6 µl, about 0.7 µl, about 0.8 µl, about 0.9 µl, about 1 µl, about 1.5 µl, about 2 µl, about 2.5 µl, about 3 µl, about 3.5 µl, about 4 µl, about 4.5 µl, about 5 µl about 6 µl, about 7 µl, about 8 µl, about 9 µl, about 10 µl, about 15 µl, about 20 µl, about 25 µl, about 50 µl, about 75 µl, about 100 µl, about 125 µl, about 150 µl, about 175 µl or even about 200 µl.

In some embodiments, the volume of the payload may be in a range of about 0.01 µl to about 200 µl, 0.01 µl to about 175 µl, 0.01 µl to about 150 µl, 0.01 µl to about 125 µl, 0.01 µl to about 100 µl, 0.01 µl to about 75 µl, 0.01 µl to about 50 µl, 0.01 µl to about 25 µl, 0.01 µl to about 20 µl, 0.01 µl to about 15 µl, 0.01 µl to about 10 µl, 0.01 µl to about 9 µl, 0.01 µl to about 8 µl, 0.01 µl to about 7 µl, 0.01 µl to about 6 µl, 0.01 µl to about 5 µl, 0.05 µl to about 5 µl, 0.1 µl to about 5 µl, 0.2 µl to about 5 µl.

In some embodiments, a payload may be transported from the body though the delivery part and the volume of a payload may then be about or less than about 1000 µl, about 900 µl, about 800 µl, about 700 µl, about 600 µl, about 500 µl, about 400 µl, about 300 µl, about 200 µl, about 100 µl, about 90 µl, about 80 µl, about 70 µl, about 60 µl, about 50 µl, about 40 µl, about 30 µl, about 20 µl, about 10 µl, about 7.5 µl about 5 µl, about 2.5 µl, about 2 µl, about 1.5 µl, about 1 µl or even about 0.5 µl.

In some embodiments, a payload may be transported from the body though the delivery part and the volume of a payload may then be more than about 0.5 µl, about 1 µl, about 1.5 µl, about 2 µl, about 2.5 µl, about 5 µl, about 7.5 µl, about 10 µl, about 20 µl, about 30 µl, about 40 µl, about 50 µl, about 60 µl, about 70 µl, about 80 µl, about 90 µl, about 100 µl, about 200 µl, about 300 µl, about 400 µl, about 500 µl, about 600 µl, about 700 µl, about 800 µl, about 900 µl or even about 1000 µl.

In some embodiments, a payload may be transported from the body though the delivery part and the volume of a payload may then be in a range of about 0.5 µl to about 1000 µl, 0.5 µl to about 900 µl, 0.5 µl to about 800 µl, 0.5 µl to about 700 µl, 0.5 µl to about 600 µl, 0.5 µl to about 500 µl, 1 µl to about 500 µl, 1.5 µl to about 500 µl, 2 µl to about 500 µl.

In some embodiments, the degradation rate/dissolution rate of delivery device for example the delivery part may dictate the mechanism and efficiency of delivery of the payload.

In some embodiments, the delivery part may be constructed to carry a payload, a payload to be delivered into an internal tissue of a subject. The payload may comprise one active drug substance or a combination of more than one different active drug substances, and optionally mixed with one or more pharmaceutically acceptable excipients.

Pharmaceutical Composition

In some embodiments, the delivery device may be contained in a pharmaceutical composition. In some embodiments, the pharmaceutical composition may comprise a delivery device. In some embodiments, the pharmaceutical composition comprises an active drug substance.

In some embodiments, the pharmaceutical composition may provide delivery of low permeable active drug substances.

In some embodiments, the delivery device may be contained in a pharmaceutical composition. Such composition may comprise one or more delivery devices and each delivery device may comprise a delivery part containing a payload. In some embodiments, the payload may contain an active drug substance.

In some embodiments, the pharmaceutical composition may comprise a delivery device. In some embodiments, the pharmaceutical composition may comprise a delivery device comprised of thermoplastic materials, which is stable and may facilitate efficient absorption and access to the blood stream in the internal tissue. In some embodiments, the pharmaceutical composition may comprise a delivery device comprised of thermoplastic materials, which may be stable and may facilitate efficient absorption and access to the blood stream in the gastrointestinal tissue after oral administration.

In some embodiments, the delivery device may be contained in a pharmaceutical composition for example in a capsule, a tablet or any other swallowable compositions to allow delivery of the delivery device at any site of the gastrointestinal tract to release the payload in the internal tissue and such payload may contain an active drug substance.

In some embodiments, the delivery device may be contained in a pharmaceutical composition for example in a suppository to allow delivery of the delivery device and to release the payload in the internal surface and such payload may contain an active drug substance.

In some embodiments, pharmaceutical composition may refer to capsules or tablets possible to swallow by most patients. Typically, a 000 capsule is the maximum size to swallow and the pharmaceutical composition may be aimed to be less than 10 mm at the smallest dimension and less than 26 mm at the largest dimension. In some embodiments, the pharmaceutical composition may be round and/or the dimension may be aimed to be less than 15 mm in the smallest dimension.

In some embodiments, the delivery device may be contained in for example a capsule composed with a pH dependent or a pH independent composition or optionally with a pH dependent or pH independent coat.

In some embodiments, the delivery device may be contained in for example a tablet composed with a pH dependent or pH independent coat. In some embodiments, the delivery device may be contained with adhesive materials in the pharmaceutical composition to bring the delivery device close to internal tissue facilitating the interaction of the delivery part and the internal tissue.

In some embodiments, the pharmaceutical composition is prepared for delivery by the delivery device in combination with adhesive materials.

In some embodiments, the delivery device may be contained with enhancers in the pharmaceutical composition to improve the delivery of the active drug substance in the internal tissue.

In some embodiments, the pharmaceutical composition is prepared for delivery by the delivery device in combination with enhancers.

In some embodiments, the pharmaceutical composition for oral administration may be administered in combination with food for example prunes and/or seeds etc. to improve peristaltic movements and potentially improve or speed up the correct positioning of the delivery device and the delivery part in the gastrointestinal wall.

Coating

In some embodiments, the capsule, the tablet or any other swallowable compositions may contain optionally a coat also denoted a coating. In some embodiments, the coat may comprise a pH-dependent composition to target delivery of the delivery device at any site of the gastrointestinal tract to release the payload in the internal tissue. In some embodiments, the coat may comprise a controlled pH-independent composition to target delivery of the delivery device at any site of the gastrointestinal tract to release the payload in the internal tissue.

In some embodiments, the delivery device, the body and/or the delivery part may contain optionally a coat or a coating. In some embodiments, the coat or coating may be silicone. In some embodiments, the silicone coat lowers the resistance of the delivery part to penetrate the internal surface. Silicone oil is any liquid polymerized siloxane with organic side chains. The most important member is polydimethylsiloxane. These polymers are of commercial interest because of their relatively high thermal stability and their lubricating properties.

In some embodiments, the silicone coat may include silicone selected from the group consisting of polydimethylsiloxane, Dimethicone in different viscosities from 20 cst to 30.000 cst, for example Dimethicone 20 cst, Dimethicone 100 cst, Dimethicone 350 cst, Dimethicone 1000 cst and/or Dimethicone 12500 cst. In some embodiments, the silicone coat may include silicone selected from the group consisting of dimethoxysilyldimethyl aminoethyl aminopropyl silicone, polydimethylsiloxane, dimethyl siloxane, trimethyl siloxane, cyclosiloxanes and/or siloxanes for example hexamethyldisiloxane.

Active Drug Substance

In some embodiments, an active drug substance suitable for use in the delivery devices may be a therapeutically, prophylactically and/or diagnostically active drug substance (herein also abbreviated "active drug substance").

In some embodiments, an active drug substance suitable for use in the delivery devices may be a low permeable active drug substance. In some embodiments, a delivery device may comprise one active drug substance or more than one different active drug substances. In some embodiments, the amount of the active drug substance may correspond to a daily or part of a daily therapeutic dose.

In some embodiments, a payload may include one or more active drug substances for delivery after administration. A wide range of active drug substances may be used. The active drug substances may include, but are not limited to, therapeutic active drug substances. For example, antibiotics, NSAIDs, angiogenesis inhibitors, neuroprotective agents, chemotherapeutic agents, cytotoxic agents, diagnostic agents, prophylactic agents (for example vaccines), and/or nutraceutical agents (for example vitamins, minerals, etc.), or other active drug substances that may be suitable for introduction to biological tissues.

In some embodiments, an active drug substance may be or may comprise a biologic. Examples of biologics including, but are not limited to, monoclonal antibodies, single chain antibodies, aptamers, enzymes, peptides, growth factors, hormones, fusion proteins, cytokines, therapeutic enzymes, recombinant vaccines, blood factors, and anticoagulants.

In some embodiments, an active drug substance may be a small molecule and/or organic compound with pharmaceutical activity. In some embodiments, an active drug substance may be or may comprise an anti-cancer agent, antibiotic, anti-viral agent, anesthetic, anticoagulant, inhibitor of an enzyme, steroidal agent, anti-inflammatory agent, antineoplastic agent, antigen, vaccine, antibody, decongestant, antihypertensive, sedative, birth control agent, progestational agent, anti-cholinergic, analgesic, anti-depressant, anti-psychotic, adrenergic blocking agent, diuretic, cardiovascular active agent, vasoactive agent, anti-glaucoma agent, neuroprotectant, angiogenesis inhibitor, etc.

In some embodiments, an active drug substance may be a therapeutic gene as known in the art. In some embodiments, an active drug substance may be selected from among amino acids, vaccines, antiviral agents, nucleic acids (for example, siRNA, RNAi, and microRNA agents), gene delivery vectors, interleukin inhibitors, immunomodulators, neurotropic factors, neuroprotective agents, antineoplastic agents, chemotherapeutic agents, polysaccharides, anti-coagulants, antibiotics, analgesic, anesthetics, antihistamines, anti-inflammatory agents, vitamins and/or any combination thereof.

In some embodiments, an active drug substance may be selected from suitable proteins, peptides and fragments thereof, which may be naturally occurring, synthesized or recombinantly produced. In some embodiments, an active drug substance may be or may comprise a cell. Such a delivery device may be useful for the injection of whole cells (for example, stem cells). In some embodiments, pharmaceutical compositions provide oral delivery of low permeable and/or low water soluble active drug substances such as peptides, and other biologics. In some embodiments, active drug substances suitable for use may include large molecule peptides and proteins which may otherwise require injection due to low absorption in the gastrointestinal tract.

In some embodiments, an active drug substance may be selected from various chemotherapeutic agents (for example interferon), antibiotics, antivirals, insulin and related substances, somatostatin and analogs, glucagon like peptides (for example GLP-1, exenatide, efpeglenatide), growth hormone (for example IFG, C-type natriuretic peptide and other growth factors), parathyroid hormone and analogues, anti-seizure agents, immune suppression agents and anti-parasitic agents such as various anti-malarial agents and/or mixture of protease inhibitors for treatment of for example HIV and AIDS.

In some embodiments, the active drug substance may typically be present in the payload in an amount of from 1-99% w/w, such as for example, from about 5-90% w/w, from about 5 to about 80% w/w, from about 5 to about 70% w/w, from about 5 to about 60% w/w, from about 5 to about 50% w/w, from about 5 to about 40% w/w, from about 5 to about 30% w/w, from about 5 to about 20% w/w, from about 5 to about 10% w/w.

In some embodiments, the active drug substance may be present in any of its crystalline, polymorphous, semi-crystalline, amorphous and/or polyamorphous forms. In some embodiments, the active drug substance may be present in a solid, a liquid, solid dispersed and/or an amorphous solid solution. In some embodiments, the delivery devices may be suitable for use for both water soluble as well as slightly soluble or insoluble active drug substances.

In some embodiments, the delivery devices may be suitable for use for both permeable as well as slightly permeable or low permeable active drug substances. In some embodiments, the active drug substance(s) may also be in the form of pharmaceutically acceptable salts, uncharged or charged molecules, molecular complexes, solvates or anhydrates thereof, and, if relevant, isomers, enantiomers, racemic mixtures, and mixtures thereof.

In some embodiments, the delivery devices may comprise pharmaceutically acceptable salts of any of the active drug substance(s). In some embodiments, pharmaceutically acceptable salts may refer to an active drug substance includes alkali metal salts such as, for example, sodium or potassium salts, alkaline earth metal salts such as, for example, calcium and magnesium salts, and salts with organic or inorganic acid such as, for example, hydrochloric acid, hydrobromic acid, nitric acid, sulfuric acid, phosphoric acid, citric acid, formic acid, maleic acid, succinic acid, tartaric acid, methanesulphonic acid, toluenesulphonic acid etc.

In some embodiments, solvates may refer to and include hydrates or solvates wherein other solvates than water may be involved such as, for example organic solvents like chloroform and the like. In some embodiments, the concentration of the active drug substance in the delivery device may depend on the specific active drug substance, the disease to be treated, the condition of the patient, the age and gender of the patient etc. in some embodiments, the above-mentioned active drug substances may be known active drug substances and a person skilled in the art will be able to find information as to the dosage of each active drug substance and, accordingly, will know how to determine the amount of each active drug substance in the composition of a delivery device.

General Production Materials

WO 2019/121686 discloses examples of body materials and delivery part materials that can be used for manufacture of delivery devices as disclosed herein.

In some embodiments, the delivery device may contain one material or multiple materials. If the delivery device may contain multiple materials, the materials may optionally be mixed together. More materials in the delivery device may optionally be in one specific location or in multiple specific locations in the delivery device for example in the delivery part, in the connection part and/or the body.

In some embodiments, the delivery part may for example contain an outer layer of one material or multiple materials and an inner core of the same material or another material or multiple materials.

In some embodiments, suitable preparation methods for the delivery device may include laser drilling, milling, cut-out, liquid filling, 3D printing, hot melt-processing and other methods of preparing pharmaceutical compositions. Also, a combination of one or more of the methods may be employed.

In some embodiments, where a preparation may be needed in order to make either of the following parts, the pharmaceutical composition, the delivery device, the body, the connection part, the delivery part and/or the payload either before, during or after the above-mentioned preparation steps, the preparation may also comprise separate steps such as for example wet granulation, dry granulation, melt granulation, pelletizing, curing, spray coating, electrostatic coating, dip coating, assembly, separate filling, injection molding, hot melt extrusion, 3D printing, milling, laser drilling or other forms of preparation methods.

In some embodiments, the delivery device or at least parts thereof may be prepared by loading an accurate amount of polymer into a mixer followed by an accurate amount of the active drug substance and/or plasticizer and/or other pharmaceutically acceptable excipients(s), liquid(s) if any. The mixing may then be performed to secure a homogeneous blend. In some embodiments, to improve the flowability, the blend may be granulated by for example dry granulation (such as roller compaction), melt granulation or wet granulation optionally with a suitable binder. In some embodiments, the blend may be dried and then fed into an injection molding machine for example Krauss Maffei and molded into the delivery device, body, connection part and the delivery part in one process.

In some embodiments, the pharmaceutical composition may be produced by methods that may be relatively simple and inexpensive. In some embodiments, the pharmaceutical composition may be prepared by conventional tablet compression. In some embodiments, the pharmaceutical composition may be prepared by conventional capsule filling. In some embodiments, the pharmaceutical composition may be prepared by conventional suppository molding.

Method of Action

In some embodiments, bowel movements may comprise the physical force to move the delivery device in the gastrointestinal tract and the physical force needed to position the delivery part into the intestinal wall to release the payload in the intestinal tissue. The transport across the gastrointestinal wall may be localized at the site of attachment in the gastrointestinal tract and consequently this will be the site of release of the active drug substance.

In some embodiments, the delivery device may be delivered in the stomach for delivery in the gastric wall to release the payload in the gastric tissue. In some embodiments, the delivery device may be delivered in the intestine for delivery in the intestinal wall to release the payload in the intestinal tissue. In the present context, bowel movements may be the peristaltic and fluid mucous flow in the gastrointestinal tracts and responsible for a directional flow of material in the lumen of the gastrointestinal tract. The peristaltic contractions may be initiated in the upper gastrointestinal tract and may move downward aiding the material to move downwards in the gastrointestinal tract. The contractions surround the material consisting of what has been swallowed. Materials may for example be in the form of food, tablet, capsules and/or drinks.

In some embodiments, bowel movements may provide a dynamic environment with a motion, which may ensure that a swallowed delivery device may not be able to pass through the gastrointestinal tract without being near the gastrointestinal wall. In some embodiments, bowel movements may comprise the physical force to move the delivery device in the gastrointestinal tract and the physical force needed for the delivery part to position itself in the gastrointestinal wall to release the payload in the gastrointestinal tissue.

Method of Delivery

In some embodiments, the pharmaceutical composition may be prepared for delivery of the delivery device in the mouth (for example buccal, sublingual), orally, rectally or vaginally.

In some embodiments, the pharmaceutical composition may be targeted to deliver the delivery device at any site in the gastrointestinal tract to release the payload in the gastrointestinal tissue. The delivery device may be delivered in the mouth for delivery sublingual or buccal, in stomach for delivery into the gastric wall to release the payload in the gastric tissue, the delivery device may be delivered in the intestine for delivery into the intestinal wall to release the payload in the intestinal tissue or the delivery device may be delivered rectal for delivery into the rectal wall to release the payload in the rectal tissue.

In some embodiments, the pharmaceutical composition may be prepared for oral intake, such as for example in the mouth (for example buccal, sublingual) or orally. In some embodiments, the pharmaceutical composition may be prepared for oral intake by swallowing. Accordingly, the size of the pharmaceutical composition may be in a range that allows for oral intake by swallowing.

In some embodiments, the pharmaceutical composition may be prepared for rectal or vaginal administration. In some embodiments, the delivery device may be contained in for example a suppository to allow delivery of the delivery device.

In some embodiment, the pharmaceutical composition may be targeted to deliver the delivery device in vagina for delivery into the vaginal wall to release the payload in the vaginal tissue.

Administration

In some embodiments, the delivery device may be prepared for administration to an individual in need thereof. The individual may be a subject. The individual may be a mammal, and in some embodiments the individual is a human being.

In some embodiments, a delivery device may be dimensioned and constructed to carry a payload and the payload may be delivered in an internal tissue of a subject after interaction with a delivery part protruding from the delivery device surface. In some embodiments, delivery devices and methods provided herein may be useful, in particular, in delivery of a variety of macromolecular, potent therapeutic agents, which may suffer from poor permeability across biological membranes/tissues. In some embodiments, delivery devices and methods provided herein may be useful, in particular, in delivery of a variety of biologics such as, for example, monoclonal antibodies, single chain antibodies, aptamer, enzymes, peptides, growth factors, hormones, antigens, fusion proteins, cytokines, therapeutic enzymes, recombinant vaccines, blood factors, and/or anticoagulants.

In some embodiments, internal tissues of a subject, such as a mammal (for example, human), may include any internal tissues in vagina and in the gastrointestinal (GI) tract, rectum, large or small intestine Jejunum, duodenum), stomach, esophagus, buccal or mouth tissue. As an example, a mucous membrane, including buccal mucosa, esophageal mucosa, gastric mucosa, intestinal mucosa, oral mucosa, rectal mucosa, vaginal mucosa etc., may be an internal tissue.

In some embodiments, the delivery device may be used for oral administration. In some embodiments, the pharmaceutical composition may be designed for oral administration. For example, the pharmaceutical compositions may be produced as capsules, for oral intake by swallowing one or more intact capsules of the pharmaceutical composition.

In some embodiments, the pharmaceutical composition may be designed for oral administration. For example, the pharmaceutical compositions may be produced as tablets, for oral intake by swallowing one or more intact tablets of the pharmaceutical composition.

In some embodiments, the pharmaceutical composition may be designed for rectal or vaginal administration. For example, the pharmaceutical compositions may be produced as suppository.

In some embodiments, the pharmaceutical composition may comprise one active drug substance or more than one different active drug substances.

In some embodiments, the pharmaceutical composition may contain one delivery device or more than one delivery devices.

In some embodiments, the delivery device may comprise one active drug substance or more than one different active drug substance. In some embodiments, the delivery device may contain an active drug substance. Due to the possibility of controlling the release rate of the active drug substance, the delivery device may be administered 1-6 times a day, such as 1-5 times daily, including 1-4 times, 1-3 times, 1-2 times or twice or once daily.

In some embodiments, the delivery device may contain an active drug substance. Due to the type of the active drug substance, the delivery device may be administered 1-6 times a day, such as 1-5 times daily, including 1-4 times, 1-3 times, 1-2 times or twice or once daily.

In some embodiments, the delivery device may contain an active drug substance. Due to the type of the active drug substance, the delivery device may be administered 1-8 times monthly, such as 1-6 times monthly, including 1-4 times, 1-2 times or twice or once monthly.

In some embodiments, the delivery device may contain an active drug substance. Due to the type of the active drug substance, the delivery device may be administered every 6 months or every year.

In some embodiments, the delivery device may be prepared for delivery of the desired dosage of active drug substance. The dosage may be dependent on the individual to whom the delivery device may be administered and the active drug substance.

General

All patent and non-patent references cited in the application are hereby incorporated by reference in their entirety. It should be understood that any feature and/or aspect discussed above in connections with the compounds according to the disclosure apply by analogy to the methods described herein. It should be understood that any feature and/or aspect discussed above in connections with the term "internal surface" apply by analogy to the term "internal tissue".

In order for the present disclosure to be more readily understood, certain terms are defined below. Additional definitions for the following terms and other term are set forth throughout the application.

In the present disclosure, when referring to an angle between two axes and/or an angle between an axis and a direction, the angle may be the smallest angle between the axes or the axis and the direction.

In the present disclosure, longitudinal axis may be defined as direction of a straight line between two points on the surface of the delivery device having the largest distance there between. In the present disclosure, the use of singular form "a", "an" and "the" include plural references unless the context clearly dictates otherwise.

As used in this application, the use of "or" means "and/or" unless stated otherwise.

As used herein, the term "comprise" and variations of the term such as "comprising" or "comprises" is intended to mean that the compositions and methods include the recited elements, but not excluding others.

As used in this application, the terms "about" and "approximately" are used as equivalent.

The following figures and examples are provided below to illustrate the present disclosure. They are intended to be illustrative and are not to be construed as limiting in any way.

DETAILED DESCRIPTION OF THE FIGURES

FIG. 1 shows an exemplary delivery device. The delivery device 2 has a first end 4 and a second end 6 with a longitudinal axis X_L there between, and comprising a body 8 and a delivery part 10. The body 8 extends along a body axis X_B from a first body end 12 to a second body end 14 and having a body surface 16. The delivery part comprises a first attachment part 18 having a first distal end 20 configured to position itself in an internal surface of a subject. The first attachment part 18 extends along a first axis X1, wherein a first angle V1 between the first axis X1 and the longitudinal axis X_L is less than 75 degrees. The first distal end 20 is arranged at a distance D1 from the body surface 16, wherein the distance D1 is about 1.5 mm. The first attachment part has a length L1 of about 5 mm. The first attachment part 18 comprises a first bevel surface 22 forming a cutting edge 24 extending from the first distal end 20. The first bevel surface faces away from the body surface 16 and has a first bevel normal 26 forming a first primary bevel angle VB1_1 with the first axis larger than 20 degrees. The first bevel normal 26 forms a first secondary angle VB1_2 with the longitudinal axis X_L larger than 60 degrees, for example about 85 degrees as illustrated.

The first distal end 20 of the first attachment part 18 is arranged between the first body end 12 and the second body end 14 of the body 8. The body 8 is made of a material comprising one or more thermoplastic polymers, the delivery part 10 is made of a material comprising one or more thermoplastic polymers. The first attachment part 18 and thus the delivery part 10 is made of a material comprising a biodegradable magnesium alloy.

The delivery device 2 comprises a connection part 30 arranged between the body 8 and the delivery part 10. The connection part 30 extends along a connection axis X_C. The connection axis X_C forms a first connection angle VC1 with the longitudinal axis X_L. The connection axis X_C forms a second connection angle VC2 with the first axis.

Figure 2:
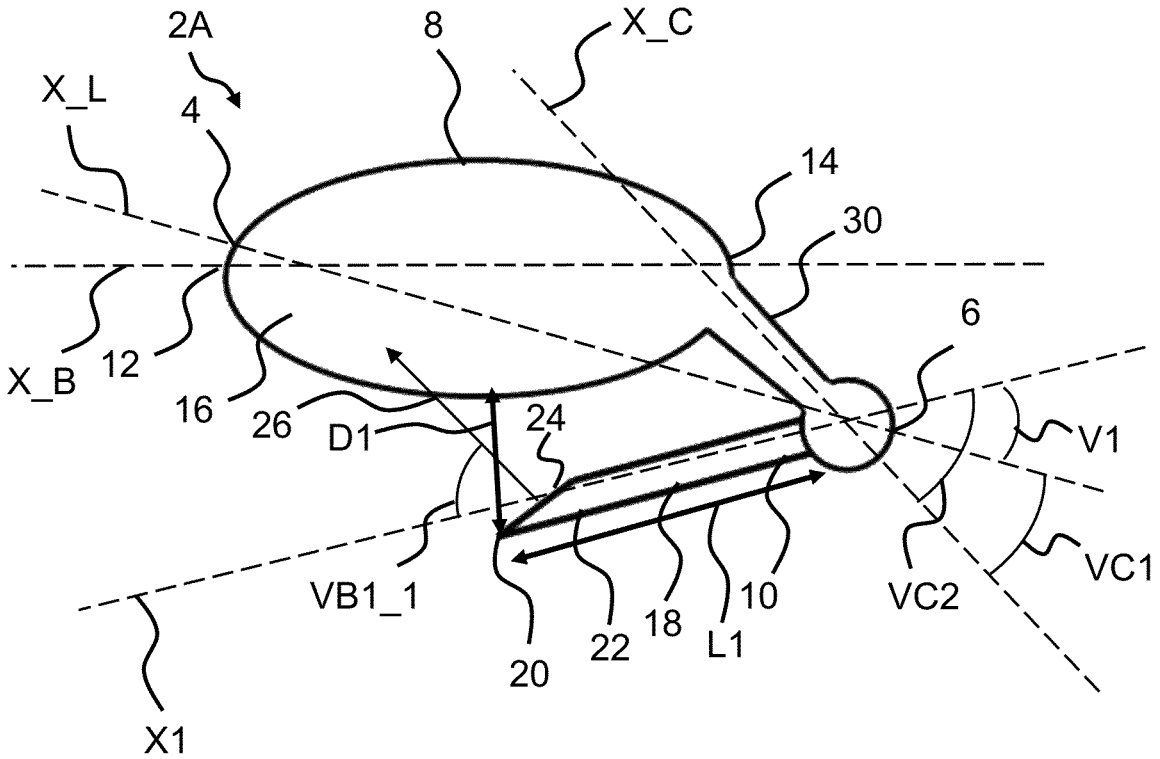
FIG. 2 schematically illustrates an exemplary delivery device

FIG. 2 shows an exemplary delivery device. The delivery device 2A has a first bevel surface 22 facing the body surface 16 with a first secondary bevel angle less than 45 degrees. The first attachment part 18 and thus the delivery part 10 is made of a material comprising a biodegradable magnesium alloy.

Figure 3:
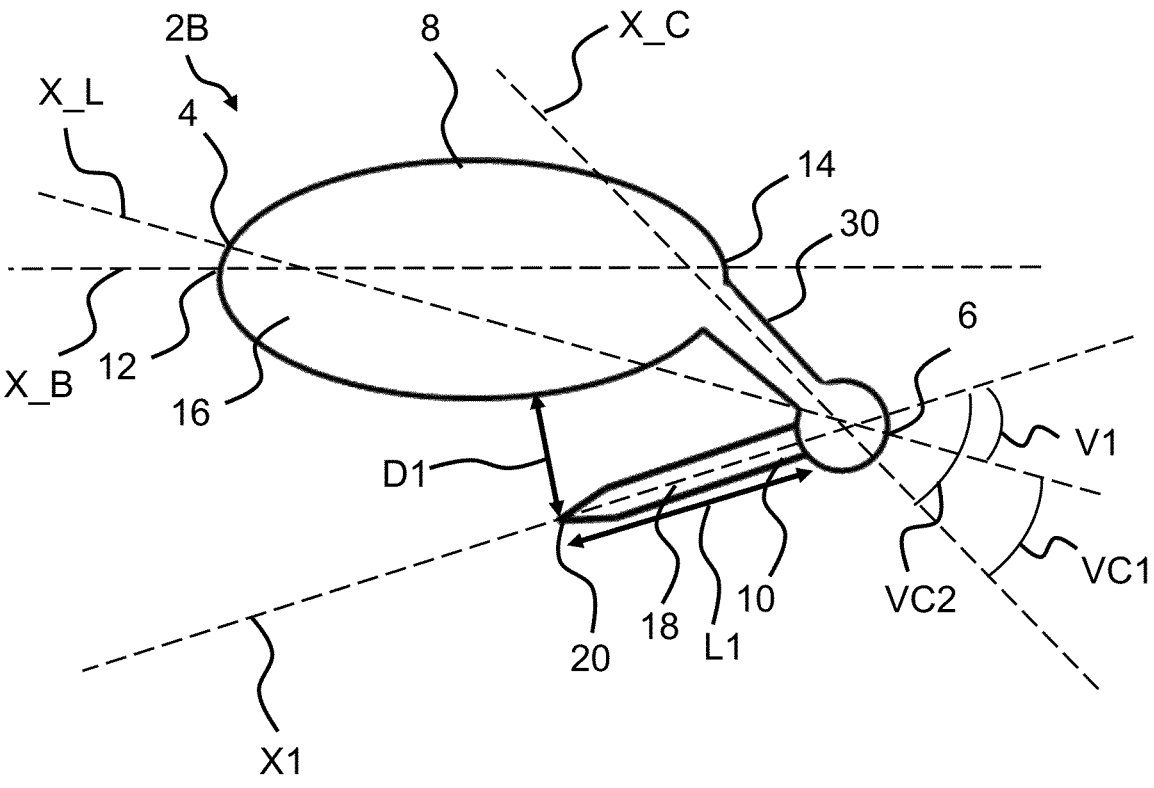
FIG. 3 schematically illustrates an exemplary delivery device

FIG. 3 shows an exemplary delivery device. The delivery device 2B has a conical tip at the first distal end 20 of the first attachment part 18. The first attachment part 18 and thus the delivery part 10 is made of a material comprising a biodegradable magnesium alloy.

Figure 4:
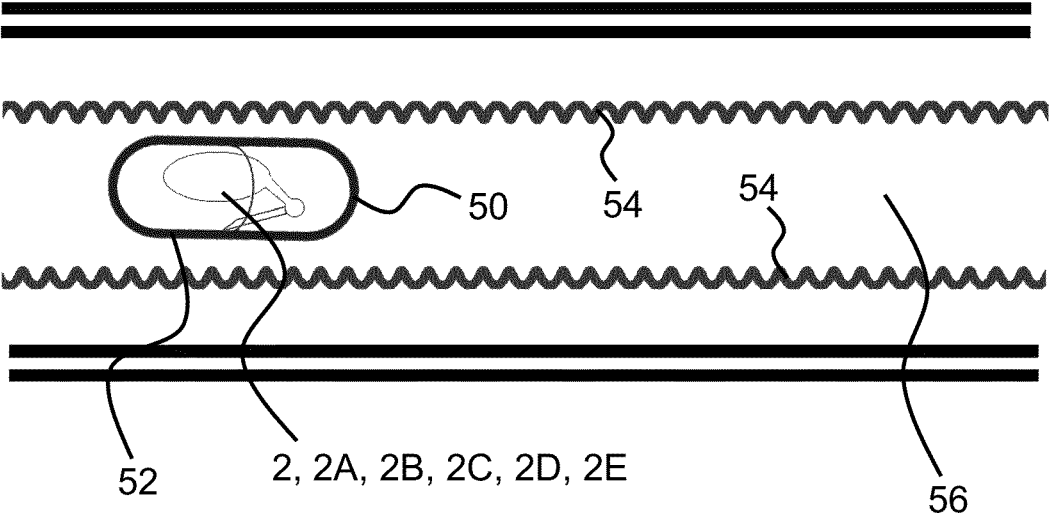
FIG. 4 illustrates a pharmaceutical composition in a gastrointestinal environment

FIG. 4 illustrates a composition in a gastrointestinal environment. The composition 50 comprise a carrier 52 and a delivery device 2A. Peristaltic movements of the gastrointestinal wall 54 moves the composition 50 in the gastrointestinal lumen 56, see also FIG. 5.

FIG. 5 illustrates the delivery device 2A in the gastrointestinal environment at a later stage. The carrier 52 has been dissolved and the delivery device 2A is pressed against the gastrointestinal wall 54 by the peristaltic movements of the gastrointestinal wall 54. The first distal end of the delivery device 2A has position itself in the inner surface of the gastrointestinal wall 54 to deliver an active drug substance to the gastrointestinal wall 54.

Figures 6, 7, 8:
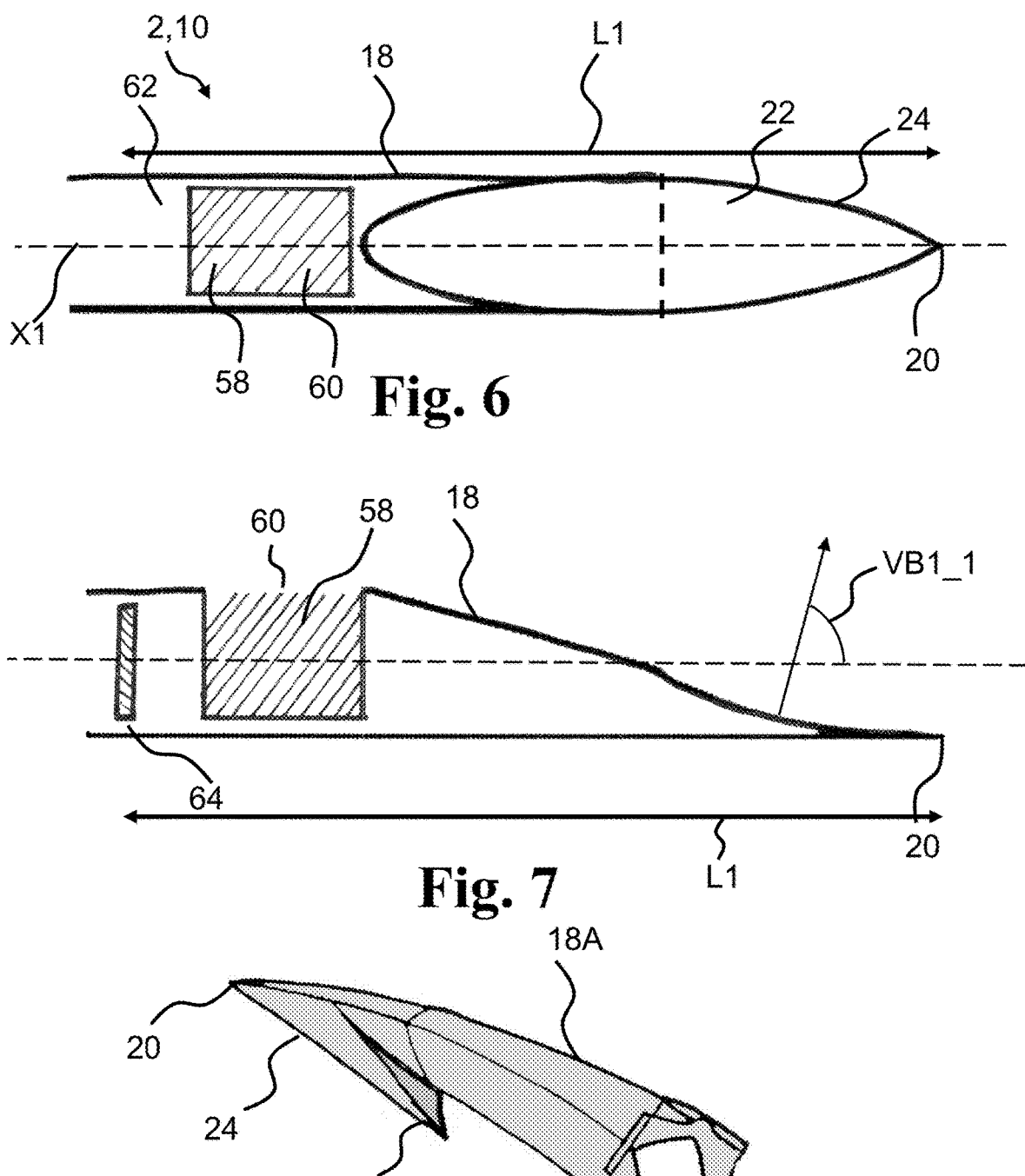
FIG. 6 is a view of an exemplary delivery part
FIG. 7 is a cross-sectional view of the delivery part of FIG. 6
FIG. 8 is a view of an exemplary attachment part

FIG. 6 is a first view of an exemplary delivery part. The delivery part 10 comprises a first attachment part 18 having a first distal end 20 configured to penetrate an internal surface of a subject. The first attachment part 18 extends along a first axis X1. The first attachment part has a length L1 of about 5 mm. The first attachment part 18 comprises a first bevel surface 22 forming a cutting edge 24 extending from the first distal end 20. The first bevel surface 22 has a first bevel normal 26 forming a first primary bevel angle VB1_1 with the first axis larger X1 than 20 degrees. The first bevel surface 22 is at least partly concave. The first attachment part 18 and thus the delivery part 10 is made of a material comprising a biodegradable metal alloy.

The exemplary first attachment part 18 defines a first cavity 58 for accommodating a payload comprising an active drug substance. The first cavity 58 may form one or more openings including a first opening 60 in the outer surface 62 of the first attachment part 10. The one or more openings in the first attachment part facilitates release of the active drug substance.

FIG. 7 is a cross-sectional view of delivery part in FIG. 6. The delivery device comprises a separation part 64 arranged between the body (not shown) and the first attachment part 18. The separation part 64 is configured to break upon attachment of the first attachment part 18 to the internal surface for separating the body and the first attachment part 18 upon attachment of the first attachment part.

FIG. 8 is a perspective view of an exemplary attachment part of a delivery device according to the present disclosure. The first attachment part 18A comprises a first barb element 66 assistive in keeping the first attachment part 18A secured or attached to the internal surface upon penetration of the internal surface. The first attachment part 18A is curved and comprises a first bend within 2 mm from the first distal end 20 such that the first distal end 20 points in a first direction (not shown) forming a first primary bend angle with the longitudinal axis and/or a first secondary bend angle with the first axis. The first attachment part 18A and thus the delivery part 10 is made of a material optionally comprising a biodegradable magnesium alloy.

Figure 9:
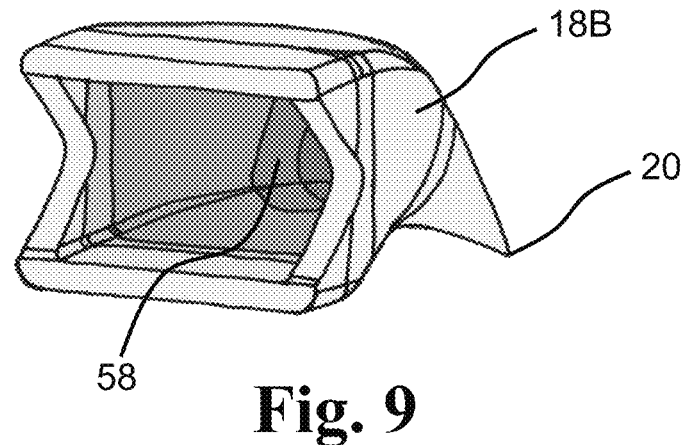
FIG. 9 is a view of an exemplary attachment part

FIG. 9 is a perspective view of an exemplary attachment part of a delivery device according to the present disclosure. The first attachment part 18B comprises a first cavity 58 extending from a distance less than 2.0 mm from the first distal end 20 assistive in keeping the first attachment part 18A secured or attached to the internal surface upon penetration of the internal surface. The first attachment part 18A is curved and comprises a first bend within 2 mm from the first distal end 20. The first attachment part 18B is made of a material optionally comprising a biodegradable magnesium alloy.

Figure 10:
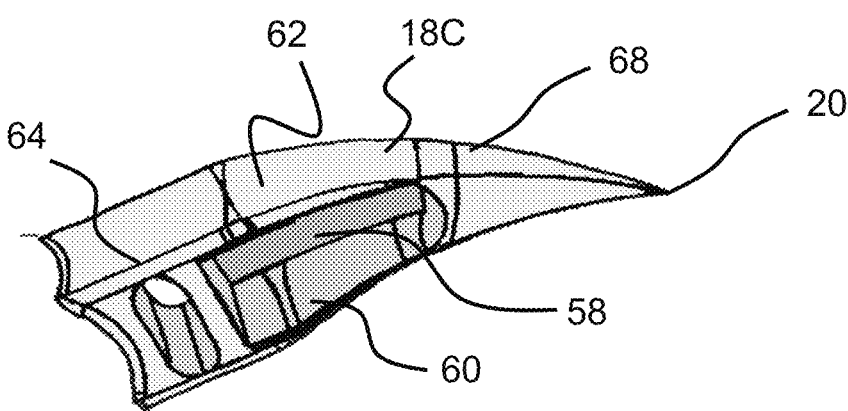
FIG. 10 is a view of an exemplary attachment part of a delivery device

FIG. 10 is a perspective view of a part of an exemplary delivery device according to the present disclosure. The delivery device comprises a first attachment part 18C comprising a first cavity 58 extending from a first opening 60 in the outer surface 62 of the first attachment part. The first attachment part 18C is curved and comprises a first bend 68 within 2 mm from the first distal end 20. A separation part 64 is formed by a through-going bore in the delivery device. The first attachment part 18C is optionally made of a material comprising a biodegradable magnesium alloy.

Figure 11:
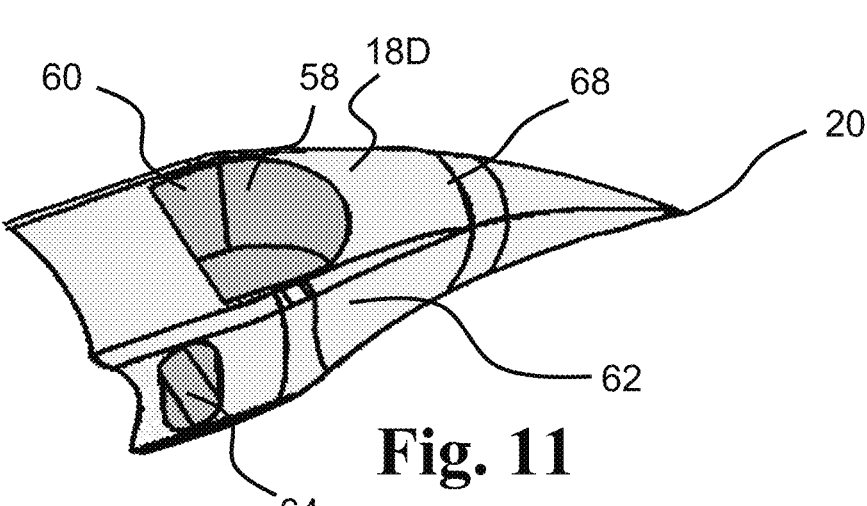
FIG. 11 is a view of an exemplary attachment part of a delivery device

FIG. 11 is a perspective view of a part of an exemplary delivery device according to the present disclosure. The delivery device comprises a first attachment part 18D comprising a first cavity 58 extending from a first opening 60 in the outer surface 62 of the first attachment part. The first attachment part 18D is curved and comprises a first bend 68 within 2 mm from the first distal end 20. A separation part 64 is formed by a through-going bore in the delivery device. The first attachment part 18D is optionally made of a material comprising a biodegradable magnesium alloy.

Figure 12:
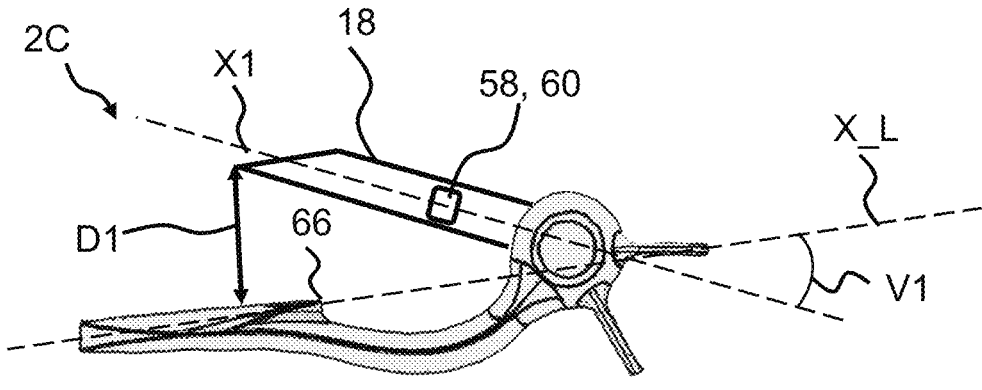
FIG. 12 is a view of an exemplary delivery device

FIG. 12 is a view of an exemplary delivery device 2C according to the present disclosure. The delivery device 2C comprises a first attachment part 18 comprising a first cavity 58 extending from a first opening 60 in the outer surface of the first attachment part. The first cavity accommodates a payload comprising an active drug substance.

Figure 13:
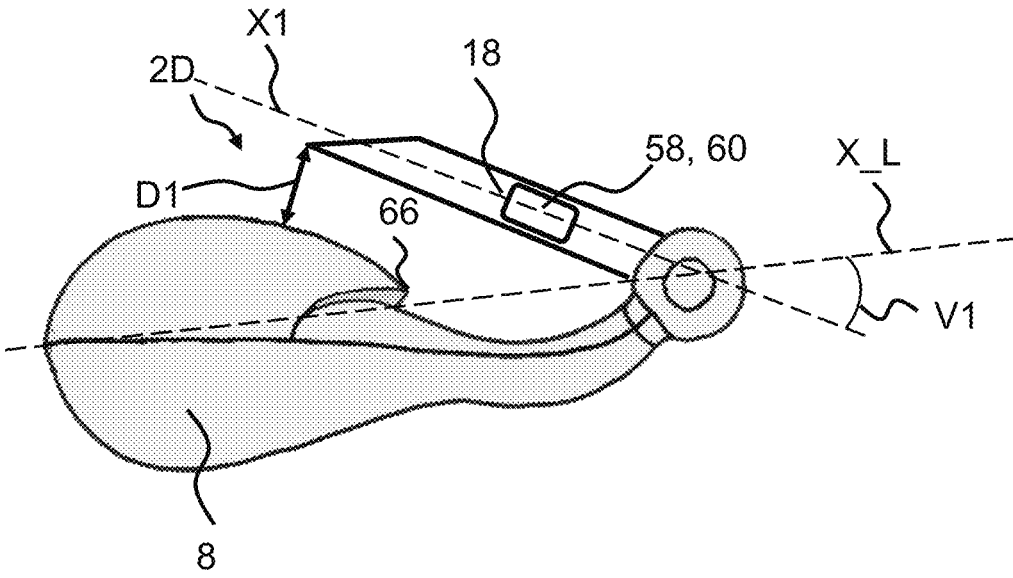
FIG. 13 is a view of an exemplary delivery device

FIG. 13 is a view of an exemplary delivery device 2D according to the present disclosure. The delivery device 2D comprises a first attachment part 18 comprising a first cavity 58 extending from a first opening 60 in the outer surface of the first attachment part 18. The first cavity 58 accommodates a payload comprising an active drug substance. The body 8 is drop-shaped and comprises a first barb element 66 assistive in keeping the delivery device 2D secured or attached to the internal surface upon penetration of the internal surface.

Figure 14:
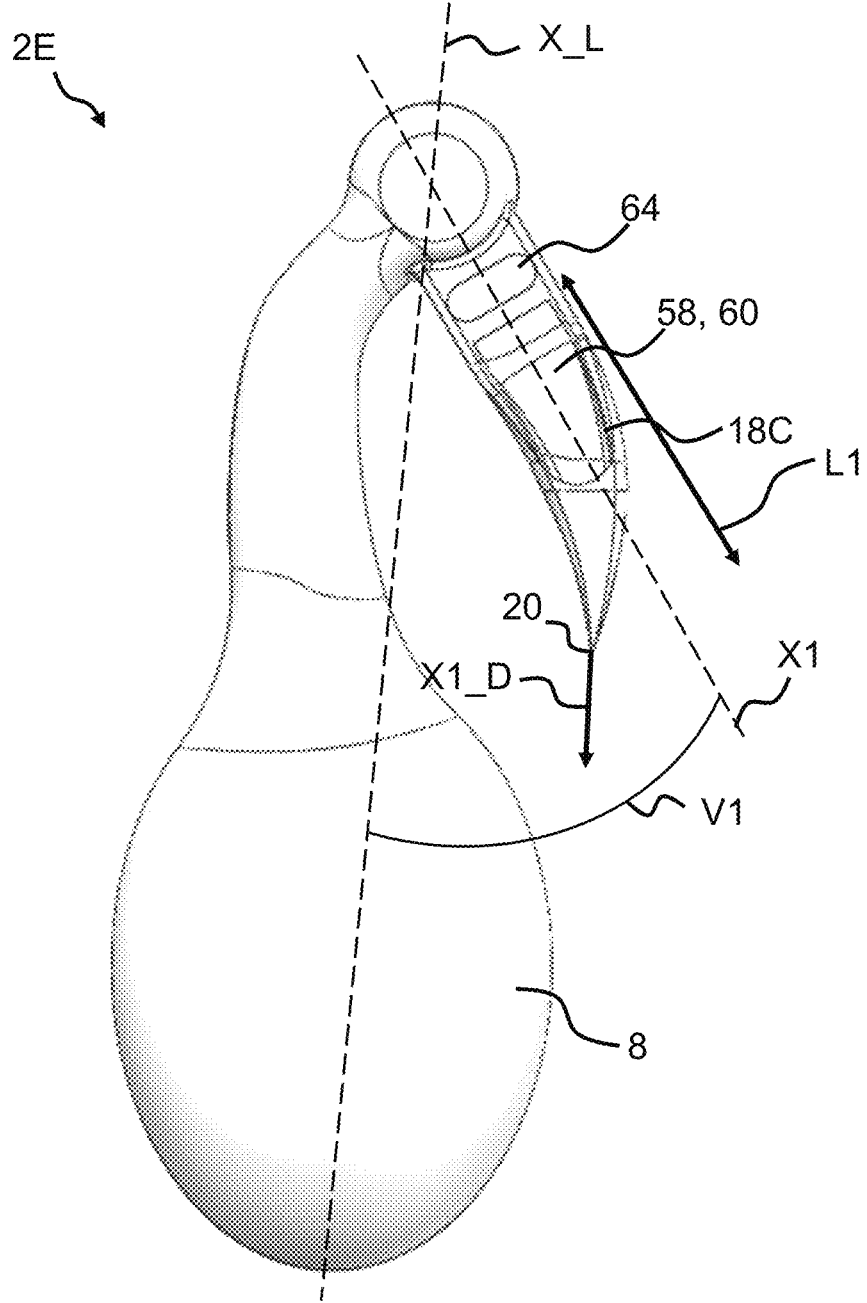
FIG. 14 is a view of an exemplary delivery device

FIG. 14 is a view of an exemplary delivery device 2E according to the present disclosure. The delivery device 2E comprises a first attachment part 18 comprising a first cavity 58 extending from a first opening 60 in the outer surface of the first attachment part 18. The first cavity 58 accommodates a payload comprising an active drug substance. The first distal end 20 points in a first direction $X1\_D$ forming a first primary bend angle with the longitudinal axis in the range from 0 to 20 degrees. The first direction $X1\_D$ forms a first secondary bend angle with the first axis $X1$ less than 60 degrees.

Parameters for exemplary delivery devices A-I are set out in Table 1.

assistive in keeping the delivery device 2F secured or attached to the internal surface upon penetration of the internal surface.

Figure 17:
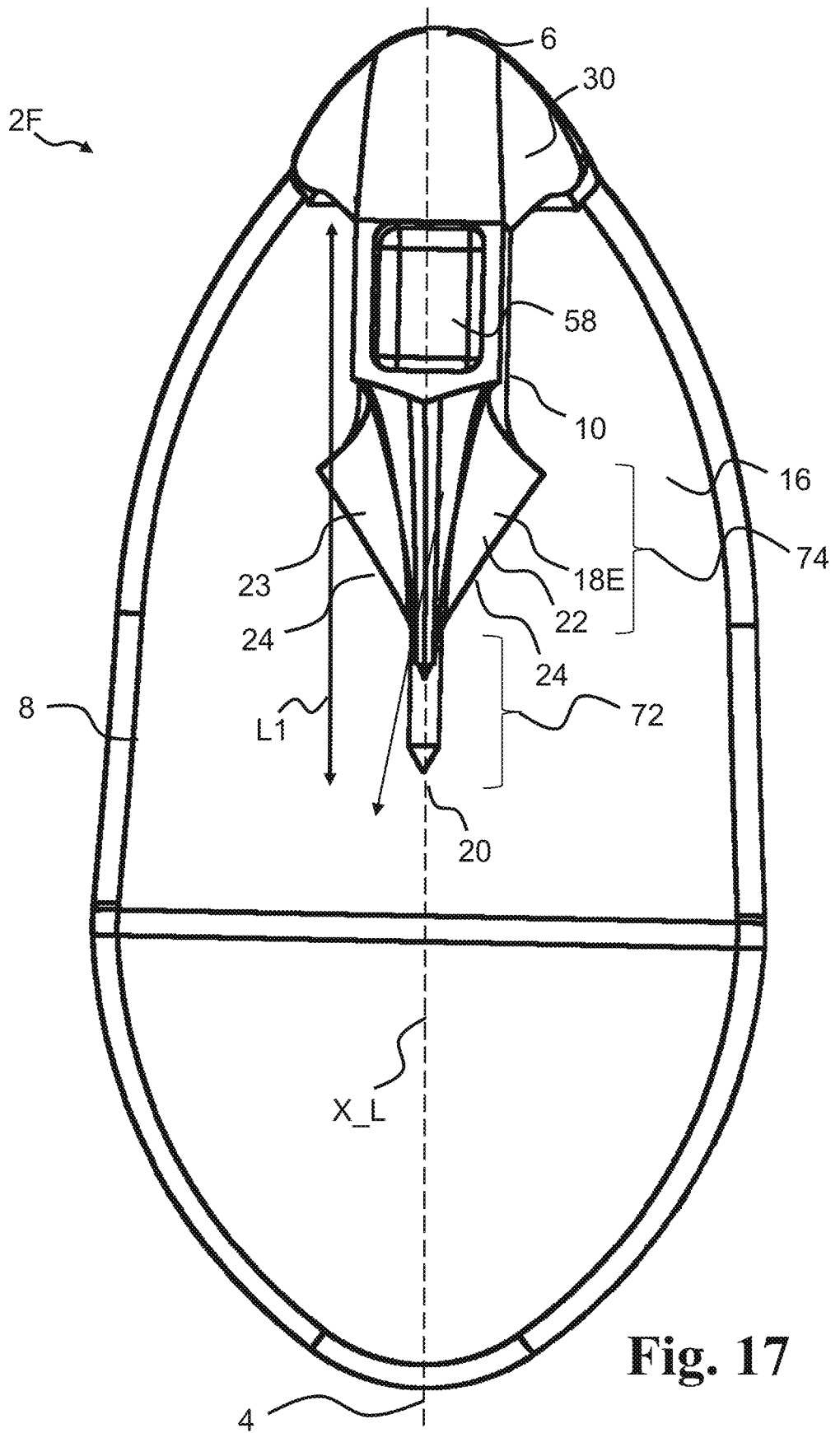
FIG. 17 is a view of an exemplary delivery device

FIG. 17 shows a side view of the delivery part 2F. The first attachment part 18E comprises second bevel surface 23 forming a cutting edge 24. The second bevel surface 23 faces away from the body surface 16. The delivery part 10 comprises first cavity 58 for accommodating a composition. The first attachment part 18E comprises a hooking zone 72 configured to hook the delivery device to the internal surface, and a cutting zone 74 configured to cut the internal surface for facilitating further penetration of the first attachment part 18E.

Figure 18:
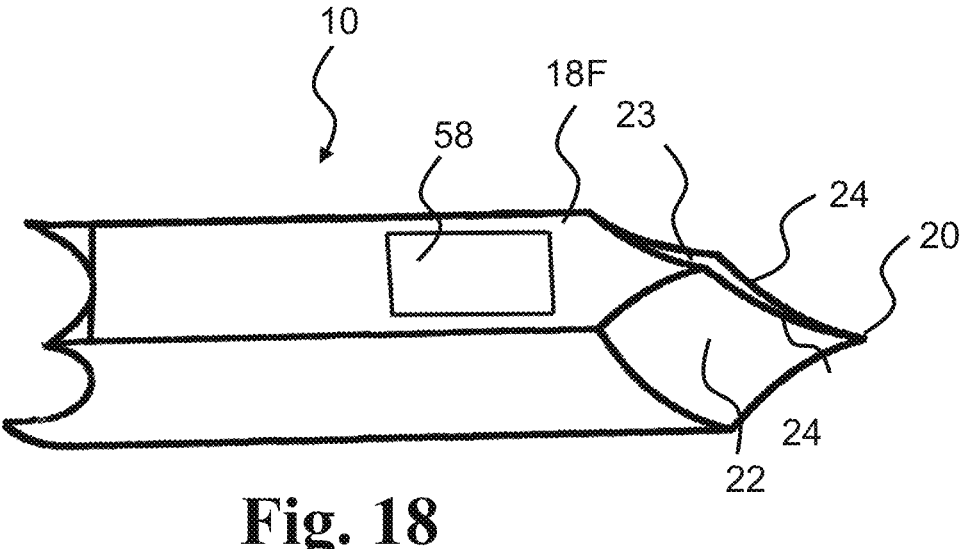
FIG. 18 is a view of an exemplary delivery part/attachment part

FIG. 18 shows a view of an exemplary delivery part 10 with first attachment part 18F. The first attachment part 18F has first bevel surface 22 and second bevel surface 23 forming cutting edges 24. The first bevel surface 22 and the second bevel surface 23 are arranged to face away from the body surface of body (not shown). The delivery part 10 comprises first cavity 58 for accommodating a composition. The first attachment part 18F is optionally made of a material comprising a biodegradable magnesium alloy.

Figure 19:
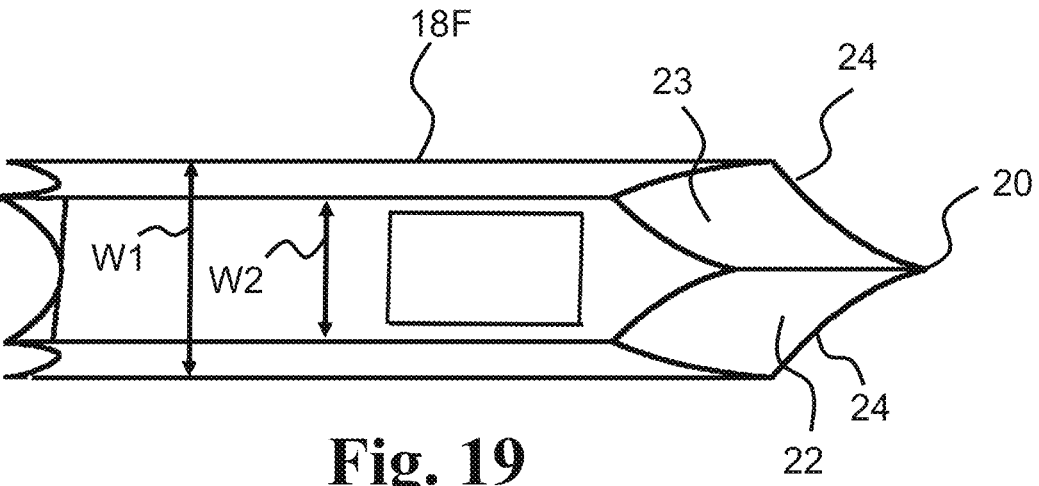
FIG. 19 is a view of an exemplary delivery part/attachment part

FIG. 19 shows a view of an exemplary delivery part 10 with first attachment part 18F. The first attachment part 18F has first bevel surface 22 and second bevel surface 23 forming cutting edges 24. The cutting edges 24 extend from the first distal end 20. The first attachment part 18F has a maximum width W1 in the range from 1.0 mm to 2.0 mm and a minimum width W2 in the range from 0.5 mm to 1.5 mm.

Figure 20:
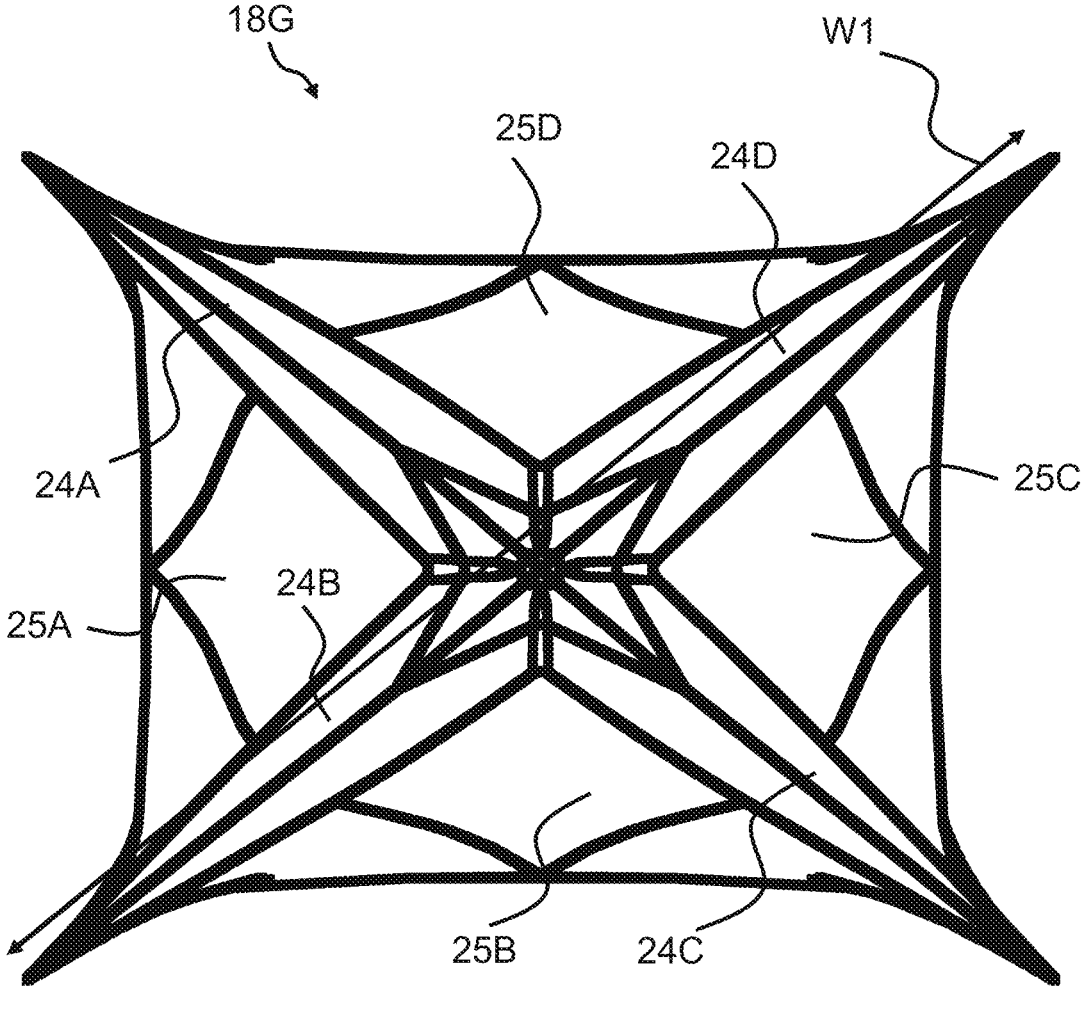
FIG. 20 is a view of an exemplary delivery part/attachment part

FIG. 20 is a distal end view of an exemplary first attachment part 18G. The attachment part 18G has a star-shaped cross-section and comprises four cutting edges 24A,

TABLE 1

|     | A | B | C | D | E | F | G | H | I |
|-----|------|------|------|------|------|-------|-------|-------|------|
| V1 (°) | 20-40 | 30-50 | 60-75 | 0-20 | 0-30 | 20-40 | 30-50 | 60-75 | 0-30 |
| D1 (mm) | 0.5-2 | 8-10 | 4-6 | 0.5-2 | 1-3 | 3-5 | 6-8 | 10-20 | 0.5-2 |
| L1 (mm) | 3-5 | 2-3 | 6-8 | 3-5 | 2-5 | 15-20 | 12-18 | 15-20 | 15-30 |

FIG. 15 shows a first end view of an exemplary delivery device 2F. The delivery device 2F has a maximum width W in the range from 2 mm to 12 mm, such as about 7 mm. The delivery device 2F comprises a body 8 and a delivery part 10. The body 8 has a body surface 16. The delivery part 10 comprises a first attachment part 18E having a first distal end 20 configured to position itself in an internal surface of a subject. The delivery device 2F has a conical tip at the first distal end 20 of the first attachment part 18E. The first attachment part 18E is optionally made of a material comprising a biodegradable metal alloy.

Figure 16:
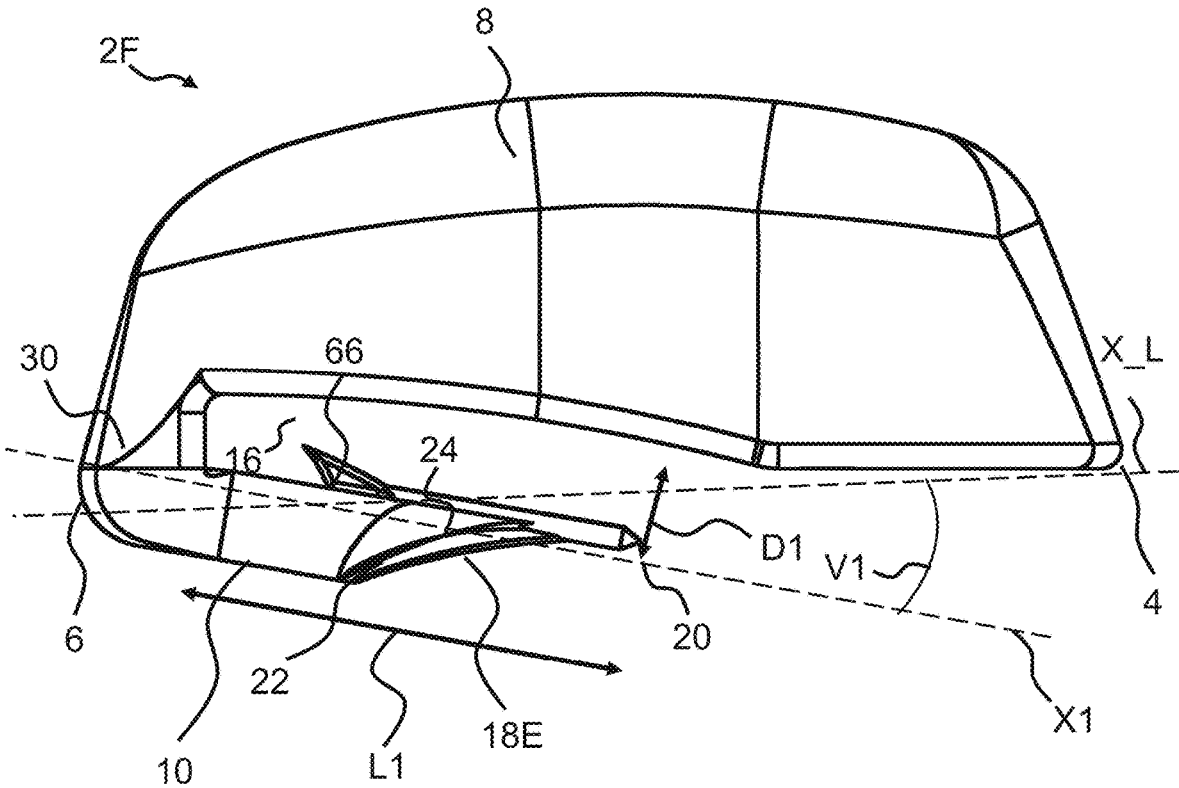
FIG. 16 is a view of an exemplary delivery device

FIG. 16 shows a side view of the delivery part 2F. The first attachment part 18E extends along a first axis $X1$, wherein a first angle V1 between the first axis $X1$ and the longitudinal axis $X\_L$ is less than 75 degrees. The first distal end 20 is arranged at a distance D1 from the body surface 16, wherein the distance D1 is in the range from 0.5 mm to 5.0 mm such as about 1.3 mm. The first attachment part 18E has a length L1 of about 5.7 mm. The first attachment part 18E comprises a first bevel surface 22 forming a cutting edge 24. The first bevel surface 22 faces away from the body surface 16. The delivery part 10 comprises a first barb element 66

24B, 24C, 24D defined by four cut-outs 25A, 25B, 25C, 25D. The first attachment part 18G has a maximum width W1 in the range from 1.0 mm to 4 mm, such as about 2.4 mm. The first attachment part 18G is optionally made of a material comprising a biodegradable magnesium alloy.

Figure 21:
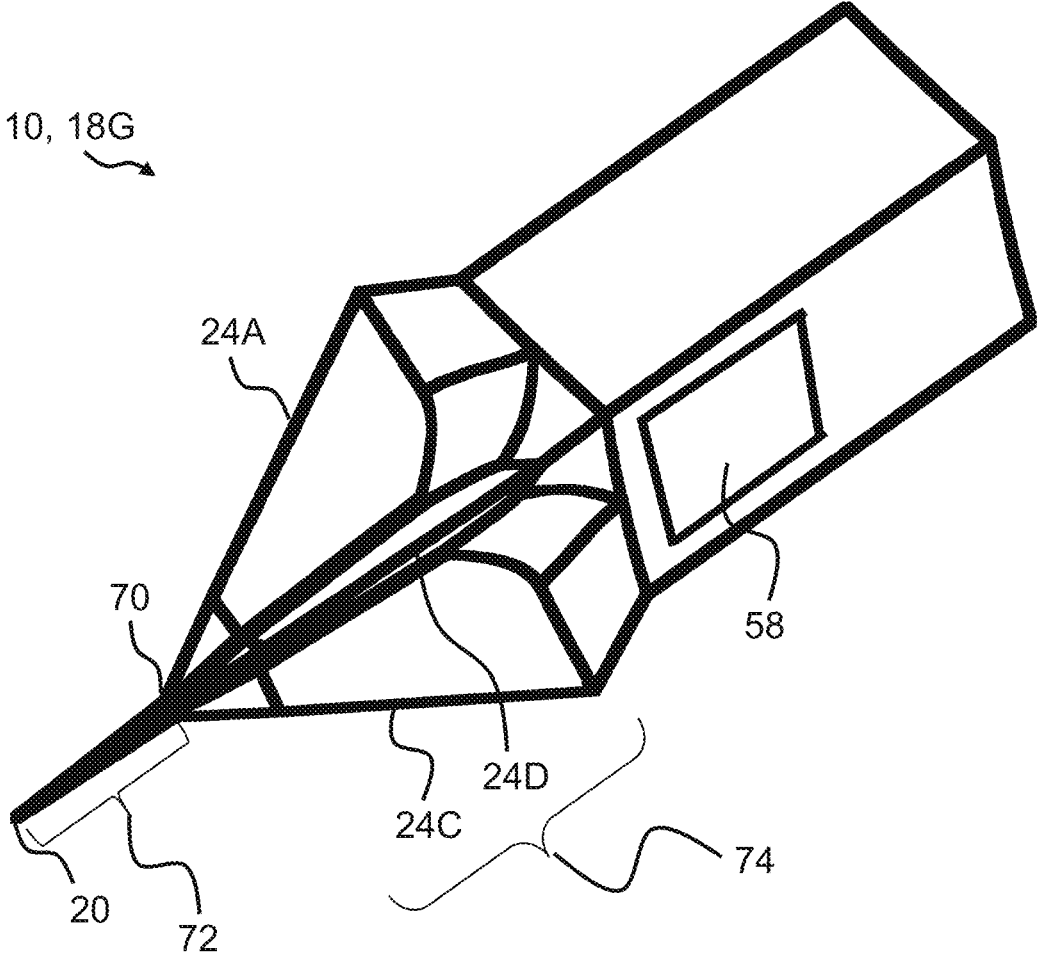
FIG. 21 is a view of an exemplary delivery part/attachment part

FIG. 21 is a view of the first attachment part 18G. The four cutting edges 24A, 24B, 24C, 24D extends from a position 70 within about 1.0 from the distal end 20 to form an initial penetration with the distal end followed by a cutting with the cutting edges when the first attachment part penetrates the internal surface.

EXPERIMENTAL RESULTS

The following provides experimental results for an example delivery device as disclosed herein. In particular, different alloys and/or coatings were tested for potential advantageous properties. The alloys and/or coatings discussed with respect to the delivery device may be incorporated into the delivery part and/or the first attachment part and/or the second attachment part.

Figure 22A:
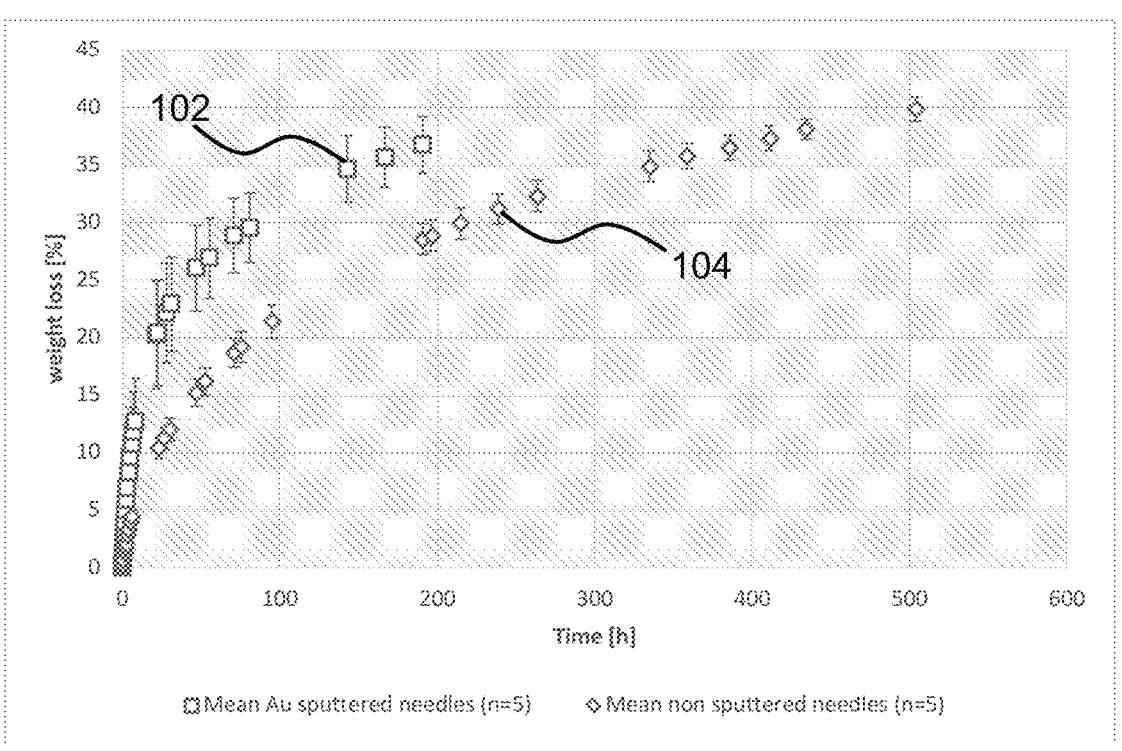
FIGS. 22A-24B is a degradation study for a RESOLOY® needle with and without gold sputtering.
Figure 22B:
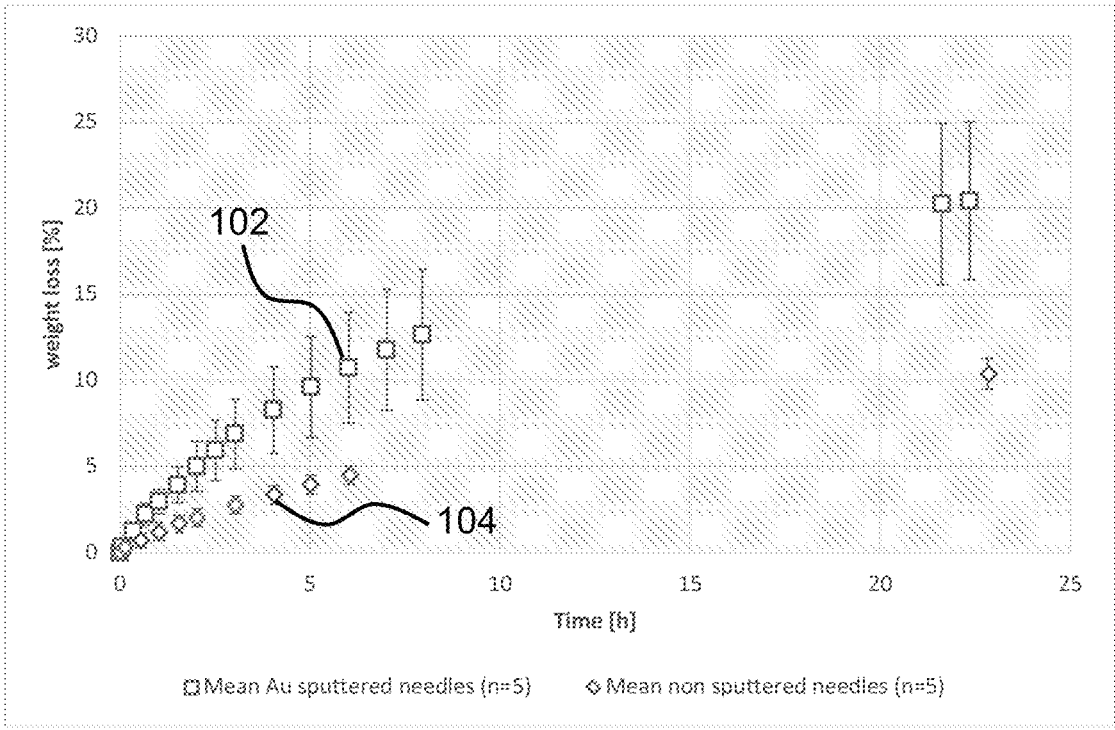

FIGS. 22A-22B illustrates the experimental results of a sputtered gold layer on a metallic needle 102 as compared to a "bare" needle having no additional layer thereon 104, comparing weight loss based on time. The tested metallic needle utilized the RESOLOY® alloy by MeKo Laser Material Processing. The RESOLOY® alloy is a mixture of dysprosium, neodymium and/or europium, zinc, zirconium, impurities, with a balance of magnesium. Further details can be found in U.S. Pat. No. 9,522,219 and/or EP2744532 B1, each of which is hereby incorporated by reference in its entirety.

The bare and sputtered gold needles were tested in a flowing phosphate buffered saline (PBS) at 37° C. having the following composition.

| | Concentration (g/L) |
|---|---|
| NaCl | 8.0 |
| KCl | 0.2 |
| $Na_2HPO_4$ | 1.15 |
| $KH_2PO_4$ | 0.2 |

As shown in FIGS. 22A-22B, the sputtered gold coating of the needle allows for significantly faster degradation as compared to the bare needle. For example, the gold-coated needle loss between 5-10% more weight than the bare needle at given times. Thus, degradation can be controlled and/or improved via the use of a coating.

Figure 23A:
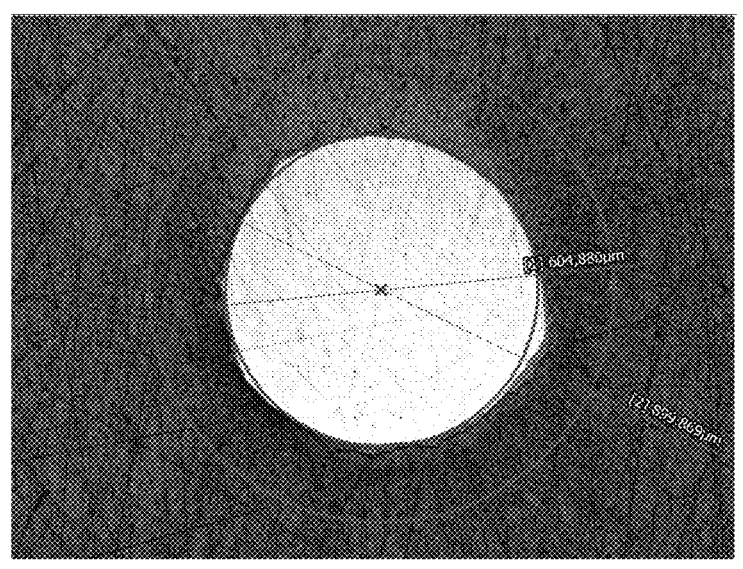
Figure 23B:
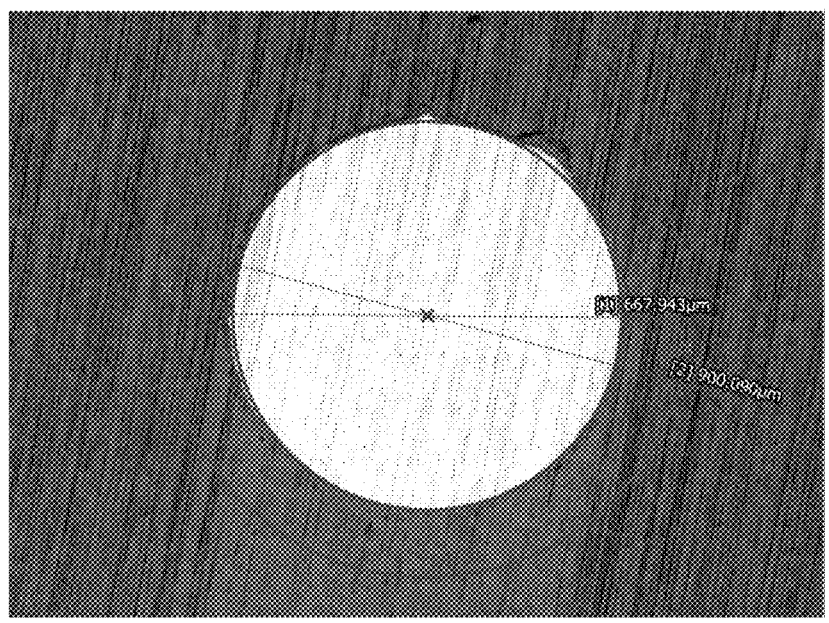

FIGS. 23A-23B illustrates cross sections of needles having undergone the degradation testing. As shown, the bare needle (FIG. 23A) undergoes a radius loss of about 150 μm within 3 weeks, leading to a degradation of about 7.2 μm per day. The gold sputtered needles (FIG. 23B) undergoes a radius loss of about 125 μm within 8 days, leading to a degradation of about 15.7 μm per day. Even faster degradation could be achieved in maximizing the surface area (for example, using a tube instead of a rod) and optimizing the coating quality. Thus, an gold-coated RESOLOY® stent with a 1.8 mm diameter and a wall thickness of 130 μm can degrade within a few hours in PBS.

Figure 24A:
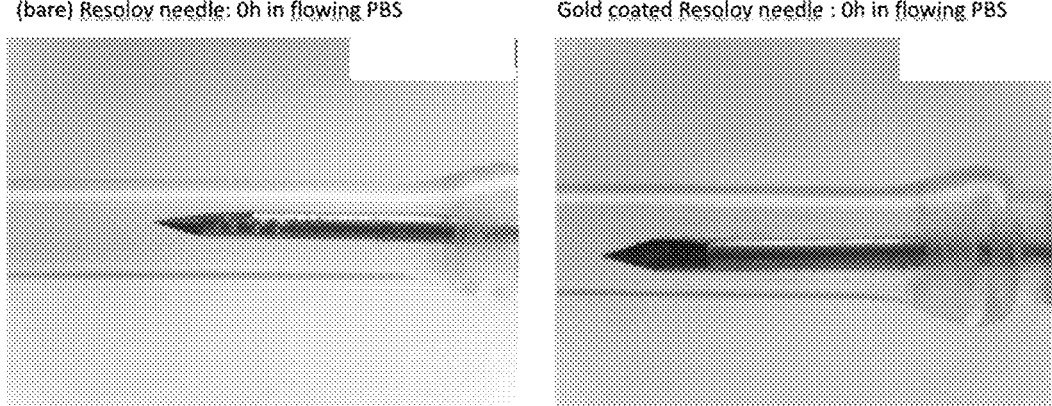
Figure 24B:
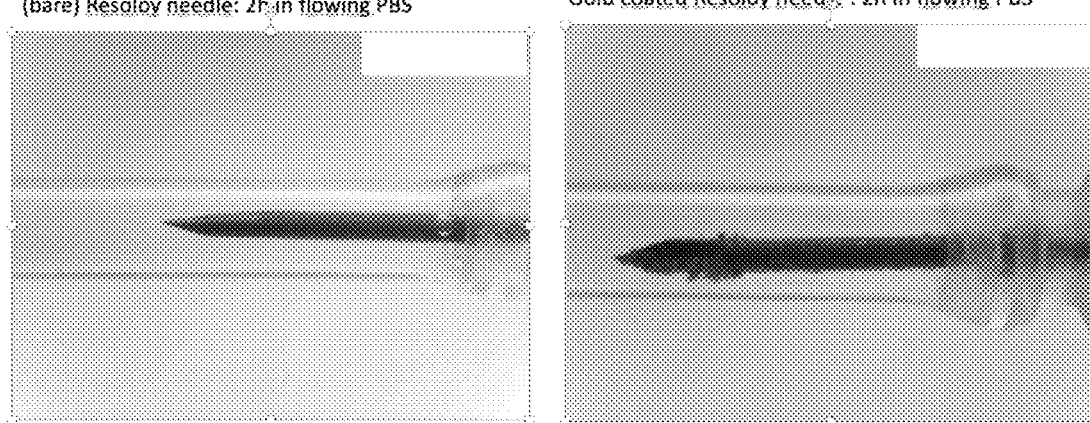

FIG. 24A illustrates a bare (left) and gold-coated (right) needle at 0 hours. FIG. 24B illustrates the same needles after 2 hours in flowing PBS. As shown, the gold-coated needle undergoes significantly more degradation.

Figure 25:
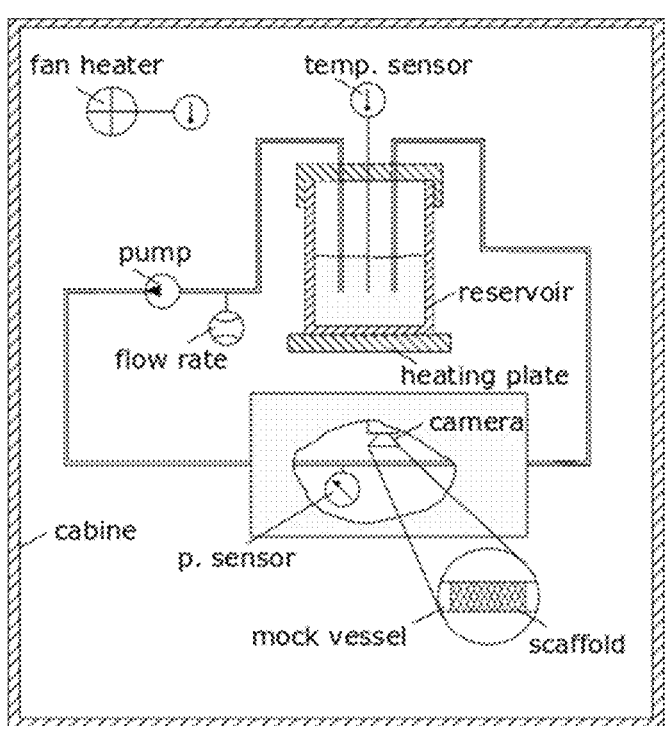
FIG. 25 illustrates a testing setup for FIGS. 22A-24B.

FIG. 25 illustrates degradation test principles and setup resulting in the above-disclosed experimental results. The dynamic (flowing) degradation test was in 37° C. PBS (pH 7.4). The fluid flow was about 120-140 ml/minute.

Figure 26:
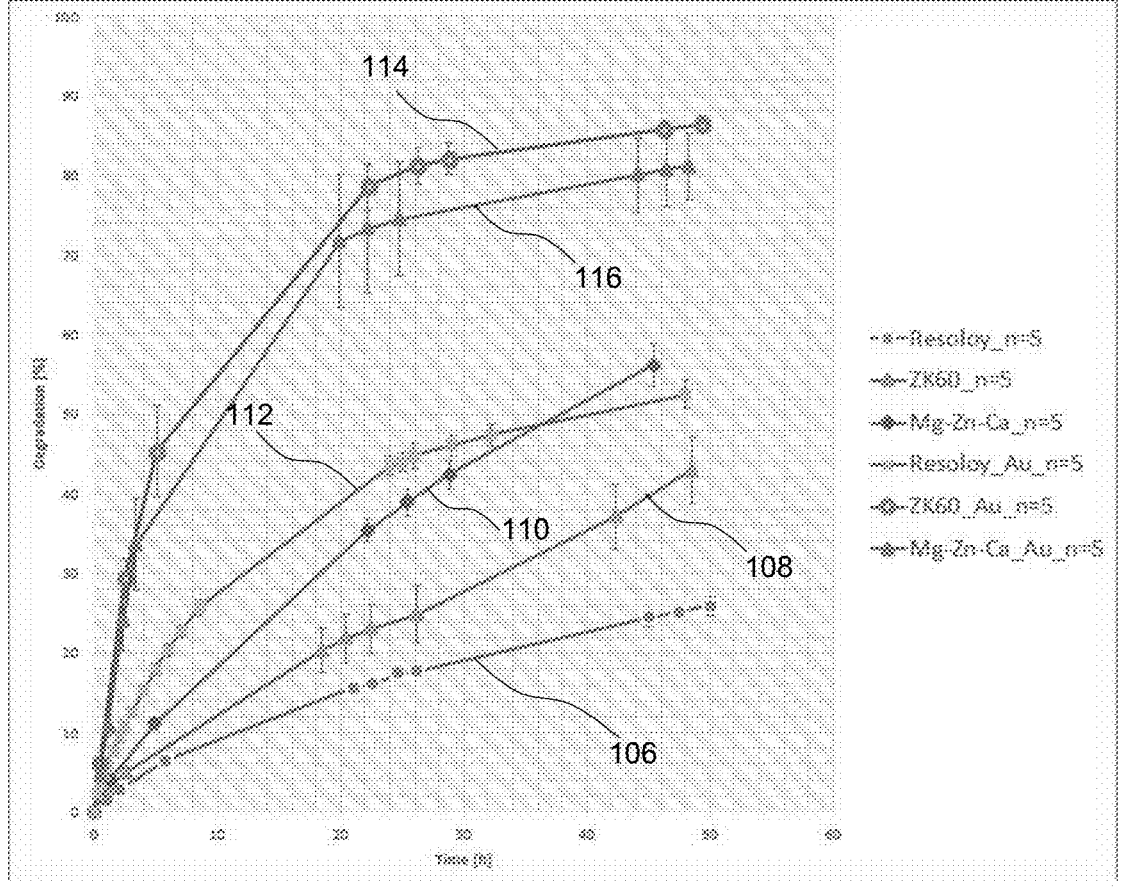
FIG. 26 is a comparative study between RESOLOY®, ZK60, and Mg—Ca—Zn tubes with and without gold sputtering.

FIG. 26 illustrates a degradation comparison between gold-sputtered and bare tubes (diameter of 0.9 mm) of RESOLOY® (106-bare, 112-Au coated), ZK60A-T5 (108-bare, 114-Au coated), and Mg—Ca—Zn (110-bare, 116-Au coated, Mg—Ca—Zn having a composition of 0.5Zn, 0.5Ca, and Mg balance). ZK60A-T5 has a composition, in wt. %, of about 94% Mg, 4.8-6.2% Zn, and >=0.45% Zr. The below table illustrates tube wall thickness without the gold sputter.

| | Wallthickness Tubes [μm] | | | |
|---|---|---|---|---|
| | Left | | Right | |
| Sample | Min | Max | Min | Max |
| 1 | 130 | 191 | 142 | 189 |
| 2 | 130 | 184 | 149 | 198 |
| 3 | 156 | 164 | 145 | 156 |
| 4 | 162 | 163 | 150 | 161 |
| 5 | 132 | 185 | 152 | 188 |

* "Right"-side was sticked into the fixture for degradation testing

As shown in FIG. 26, the degradation percentage can vary based on the materials used. Accordingly, different materials with or without the coatings may be advantageous for certain situations. For example, for a longer attachment time, it may be advantageous to use RESOLOY®. For extremely fast attachments, ZK60 with a gold coating may be advantageous. However, for some fast degrading materials, the material may be softer which can result in less sharp spike tips, leading to non-attachment. Therefore, the disclosure allows for flexibility in degradation time based on the material used.

Figure 27A:
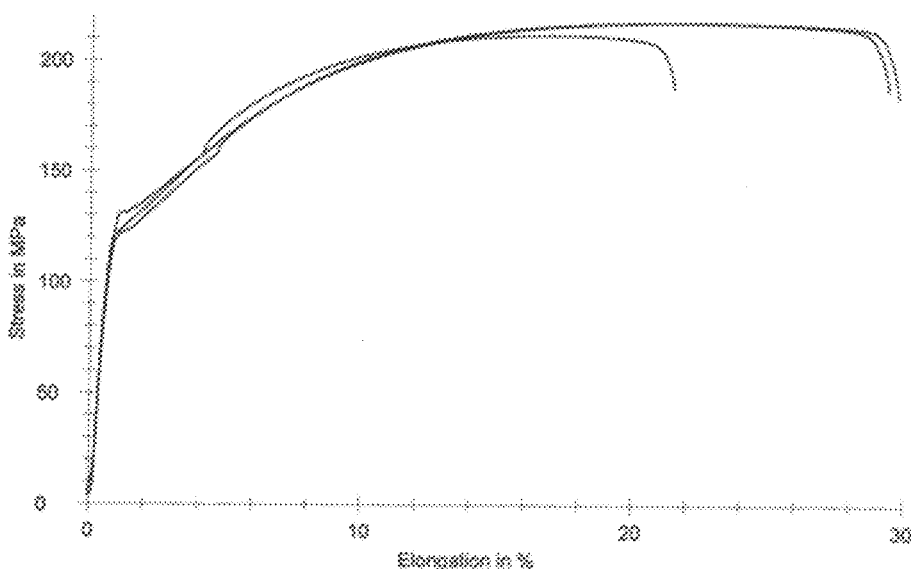
FIGS. 27A-27C illustrates stress-strain curves of RESOLOY®, ZK60, and Mg—Ca—Zn wires.
Figure 27B:
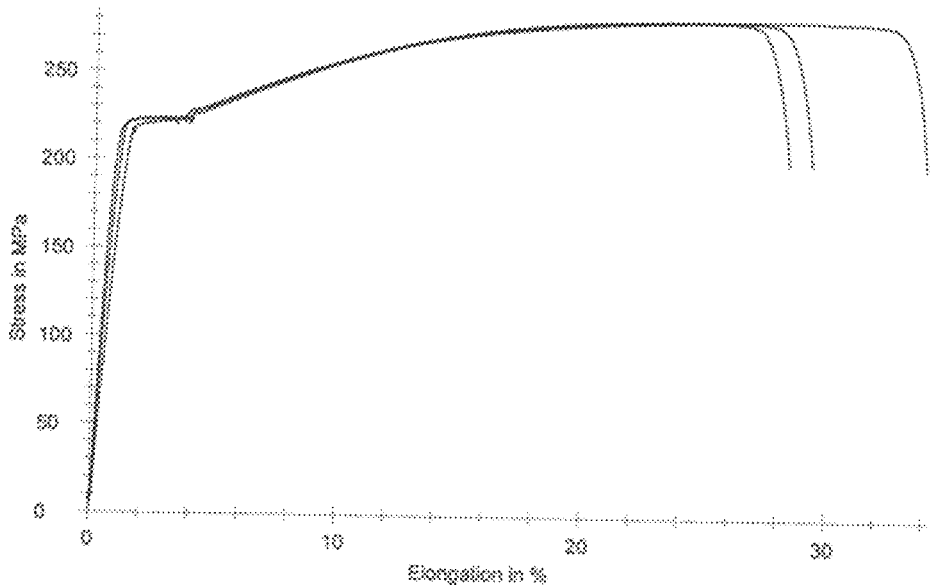
Figure 27C:
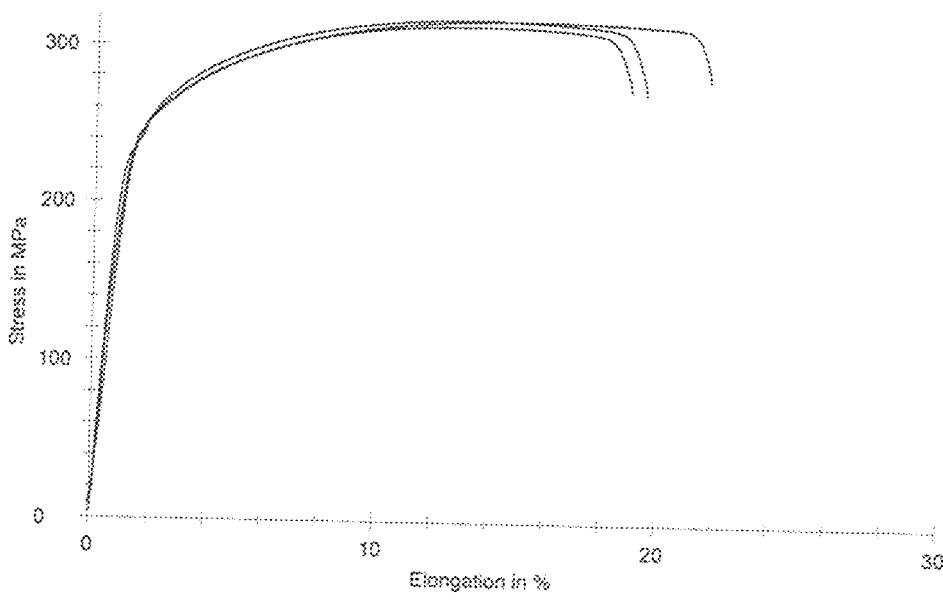

FIGS. 27A-27C illustrate stress-strain curves for different tested alloys as wires. FIG. 27A illustrates the stress-strain curve for Mg—Ca—Zn, FIG. 27B illustrates the stress-strain curve for RESOLOY®, and FIG. 27C illustrates the stress-strain curve for ZK60A-T5.

Figure 28:
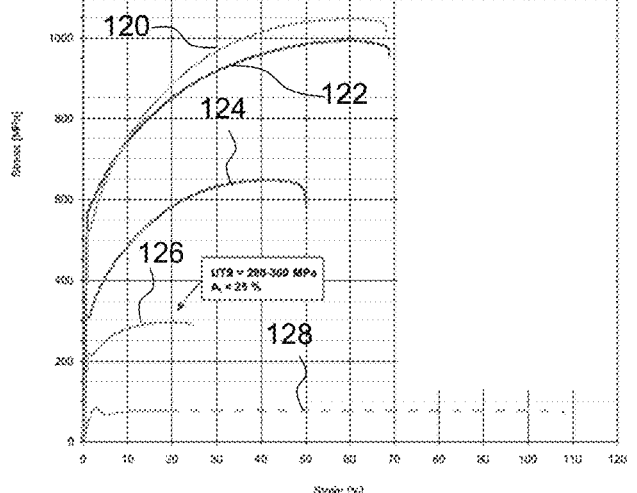
FIG. 28 illustrates mechanical properties of RESOLOY® in comparison to other stent materials.
Figure 28:
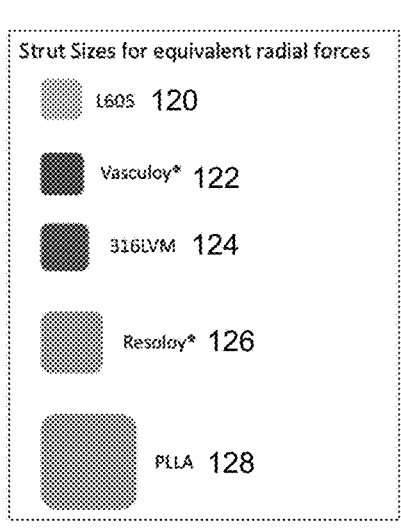

FIG. 28 illustrates mechanical properties of RESOLOY® in comparison to other stent materials. Specifically, FIG. 28 shows a comparison of L605 (non-magnetic chromium, nickel, tungsten, cobalt alloy) (120), Vasculoy® (112), 316LVM (124), RESOLOY® (126), and polylactic acid (PLLA) (122).

The below figure illustrates the heavy metal content in RESOLOY® testing in a wire.

| Parameter | Amount (μg/g) |
|---|---|
| Cd | <0.5 |
| Pb | <2 |
| As | <5 |
| Hg | <0.5 |
| Co | <1 |
| V | <1 |
| Ni | 15 |
| Ti | <1 |
| Au | <1 |
| Pd | <1 |
| Ir | <1 |
| Os | <1 |
| Rh | <1 |
| Ru | <1 |
| Se | <5 |
| Ag | <1 |
| Pt | <1 |
| Li | <1 |
| Sb | <1 |
| Ba | <1 |
| Mo | <2 |
| Cu | 9.7 |
| Sn | 1.6 |
| Cr | 5.5 |

Also disclosed are delivery devices, methods, and compositions according to any of the following items.

Item 1. A delivery device for a composition, the delivery device having a first end and a second end, the delivery device comprising a body and a delivery part, the body extending along a body axis from a first body end and having a body surface, the delivery part comprising a first attachment part, the first attachment part having a first distal end configured to position itself in an internal surface of a subject, wherein the delivery part is made of material comprising one or more of magnesium, iron and zinc.

Item 2. Delivery device according to item 1, wherein the material of the delivery part comprises a magnesium alloy.

Item 3. Delivery device according to any of items 1-2, wherein the material of the delivery part is biocompatible and/or biodegradable.

Item 4. Delivery device according to any of items 1-3, wherein the first attachment part is made of material comprising one or more of magnesium, iron and zinc.

Item 5. Delivery device according to any of items 1-4, wherein the first attachment part is made of material comprising one or more polymers.

Item 6. Delivery device according to any of items 1-5, wherein the first attachment part comprises a metallic coating and/or a polymer coating.

Item 7. Delivery device according to any of items 1-6, wherein the first attachment part comprises a first barb.

Item 8. A method of manufacture of a delivery device comprising a body and a delivery part, the body extending along a body axis from a first body end and having a body surface, the method comprising:

providing a delivery part, wherein providing a delivery part comprises forming a first attachment part by laser-cutting of a delivery part member; and attaching the delivery part to the body.

Item 9. Method according to item 8, wherein the delivery part member is made of material comprising one or more of magnesium, iron and zinc.

Item 10. Method according to any of items 8-9, wherein forming a first attachment part comprises forming a first barb in the delivery part member.

Item 11. Delivery device according to any of items 1-7, the delivery device having a longitudinal axis between the first end and the second end thereof, wherein the first attachment part extends along a first axis, wherein a first angle between the first axis and the longitudinal axis is less than 75 degrees.

Item 12. Delivery device according to any of items 1-7 and 11, the first distal end being arranged at a distance from the body surface, wherein the distance is at least 0.5 mm.

Item 13. Delivery device according to any of items 1-7 and 11-12, wherein the first attachment part has a length in the range from 1.0 mm to 20 mm.

Item 14. Delivery device according to any of items 1-7 and 11-13, wherein the first attachment part comprises a first bevel surface forming a cutting edge extending from the first distal end.

Item 15. Delivery device according to item 14, wherein the first bevel surface is concave.

Item 16. Delivery device according to any of items 14-15, wherein the first bevel surface has a first bevel normal, the first bevel normal forming a first primary bevel angle with the first axis larger than 20 degrees.

Item 17. Delivery device according to any of items 14-16, wherein the first bevel surface has a first bevel normal, the first bevel normal forming a first secondary angle with the longitudinal axis larger than 45 degrees.

Item 18. Delivery device according to any of items 1-17, wherein the first attachment part comprises a second bevel surface forming a cutting edge at the first distal end.

Item 19. Delivery device according to item 18, wherein the second bevel surface is concave.

Item 20. Delivery device according to any of items 1-7 and 11-19, wherein the first attachment part defines a first cavity for accommodating a payload comprising an active drug substance.

Item 21. Delivery device according to any of items 1-7 and 11-20, the delivery part comprising a second attachment part, the second attachment part having a second distal end configured to position itself in an internal surface of a subject, the second distal end being arranged at a distance from the body surface, wherein the distance is at least 0.5 mm.

Item 22. Delivery device according to any of items 1-7 and 11-21, wherein the first distal end of the first attachment part is arranged between the first body end and a second body end of the body.

Item 23. Delivery device according to any of items 1-7 and 11-22, wherein the body is made of a material comprising one or more thermoplastic polymers.

Item 24. Delivery device according to any of items 1-7 and 11-23, wherein the delivery part is made of material comprising one or more thermoplastic polymers.

Item 25. Delivery device according to any of items 1-7 and 11-24, wherein a material of the first attachment part comprises one or more active drug substances.

Item 26. Delivery device according to any of items 1-7 and 11-25, wherein the delivery device comprises a separation part arranged between the body and the first attachment part, wherein the separation part is configured to break upon attachment of the first attachment part to the internal surface for separating the body and the first attachment part upon or after attachment of the first attachment part.

Item 27. Delivery device according to any of items 1-7 and 11-26, wherein the body has a droplet shape with a wide end towards the first body end.

Item 28. A composition comprising a carrier and a delivery device according to any of items 1-7 and 11-27.

Item 29. Composition according to item 28, wherein the composition is an oral composition.

Item 30. Composition according to any of items 28-29, wherein the composition is a pharmaceutical composition comprising an active drug substance.

Item 31. Composition according to item 30, wherein the composition comprises a payload with the active drug substance, wherein the payload is accommodated in a cavity of the delivery device.

LIST OF REFERENCES 2, 2A, 2B, 2C, 2D, 2E, 2F delivery device
4 first end
6 second end
8 body
10 delivery part
12 first body end
14 second body end
16 body surface
18, 18A, 18B, 18C, 18D, 18E, 18F, 18G first attachment part
20 first distal end
22 first bevel surface
23 second bevel surface
24, 24A, 24B, 24C, 24D cutting edge
25, 25A, 25B, 25C, 25D cut-outs
26 first bevel normal
30 connection part
50 composition
52 carrier
54 gastrointestinal wall
56 gastrointestinal cavity
58 first cavity
60 first opening in first attachment part
62 outer surface of first attachment part
64 separation part
66 first barb element
68 first bend
70 position where the cutting edges extend from
72 hooking zone
74 cutting zone 37 38

102 mean Au sputtered needles
104 mean non-sputtered needles
106 RESOLOY® without Au
108 ZK60 without Au
110 Mg—Zn—Ca without Au
112 RESOLOY® with Au
114 ZK60 with Au
116 Mg—Zn—Ca with Au
120 L605
122 Vaculoy®
124 316LVM
126 RESOLOY®
128 PLLA
X_L longitudinal axis
X_B body axis
X_C connection axis
X1 first axis
X2 second axis
X1_D first direction
L1 length of first attachment part
D1 distance between the first distal end and the body surface
V1 first angle between first axis and longitudinal axis
VB1_1 first primary bevel angle
VB1_2 first secondary bevel angle
VC1 first connection angle
VC2 second connection angle
W1, W2 width

The invention claimed is:

1. A delivery device for a swallowable composition, the delivery device comprising:
   a first end and a second end, the delivery device comprising:
      a body; and
      a delivery part, the body extending along a body axis from a first body end to a second body end and having a body surface, the delivery part comprising a first attachment part, the first attachment part having a first distal end configured to position itself in an internal surface of a subject, the first distal end of the first attachment part is arranged between the first body end and the second body end of the body;
   wherein the internal surface of the subject is in an organ selected from the esophagus, stomach, duodenum, small intestine, caecum, large intestine, colon, rectum; and
   wherein the delivery part is made of material comprising one or more of magnesium, iron and zinc.

2. The delivery device according to claim 1, wherein the material of the delivery part comprises a magnesium alloy.

3. The delivery device according to claim 1, wherein the material of the delivery part is biocompatible and/or biodegradable.

4. The delivery device according to claim 1, wherein the first attachment part is made of material comprising one or more of magnesium, iron and zinc.

5. The delivery device according to claim 1, wherein the first attachment part is made of material comprising one or more polymers.

6. The delivery device according to claim 1, wherein the first attachment part comprises a metallic coating and/or a polymer coating.

7. The delivery device according to claim 1, wherein the first attachment part comprises a first barb.

8. The delivery device according to claim 1, the delivery device having a longitudinal axis between the first end and the second end thereof, wherein the first attachment part extends along a first axis, wherein a first angle between the first axis and the longitudinal axis is less than 75 degrees.

9. The delivery device according to claim 8, the first distal end being arranged at a distance from the body surface, wherein the distance is at least 0.5 mm.

10. The delivery device according to claim 1, wherein the first attachment part has a length in the range from 1.0 mm to 20 mm.

11. The delivery device according to claim 1, wherein the first attachment part comprises a first bevel surface forming a cutting edge extending from the first distal end.

12. The delivery device according to claim 1, wherein the first attachment part defines a first cavity for accommodating a payload comprising an active drug substance.

13. The delivery device according to claim 1, wherein the delivery part is made of material comprising one or more thermoplastic polymers.

14. The delivery device according to claim 1, wherein a material of the first attachment part comprises one or more active drug substances.

15. The delivery device according to claim 1, wherein the delivery device comprises a separation part arranged between the body and the first attachment part, wherein the separation part is configured to break upon attachment or after attachment of the first attachment part to the internal surface thereby separating the body and the first attachment part upon or after attachment of the first attachment part to the internal surface.

16. An oral composition comprising a carrier and a delivery device according to claim 1, wherein the composition is a pharmaceutical composition comprising an active drug substance.

17. The delivery device according to claim 1, wherein the first attachment part is offset from the body.

18. A delivery device for a composition, the delivery device comprising:
   a first end and a second end, the delivery device comprising:
      a body; and
      a delivery part, the body extending along a body axis from a first body end and having a body surface, the delivery part comprising a first attachment part, the first attachment part having a first distal end configured to position itself in an internal surface of a subject;
   wherein the delivery part is made of material comprising one or more of magnesium, iron and zinc; and
   wherein the delivery device comprises a separation part arranged between the body and the first attachment part, wherein the separation part is configured to break upon attachment or after attachment of the first attachment part to the internal surface thereby separating the body from the first attachment part upon or after attachment of the first attachment part to the internal surface.

* * * * *